(12) United States Patent
Kalechofsky et al.

(10) Patent No.: US 9,014,785 B2
(45) Date of Patent: *Apr. 21, 2015

(54) TECHNIQUES, SYSTEMS AND MACHINE READABLE PROGRAMS FOR MAGNETIC RESONANCE

(71) Applicant: Millikelvin Technologies LLC, Braintree, MA (US)

(72) Inventors: Neal Kalechofsky, Stow, MA (US); Mirko Hrovat, Brockton, MA (US)

(73) Assignee: Millikelvin Technologies LLC, Braintree, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/188,410

(22) Filed: Feb. 24, 2014

(65) Prior Publication Data

US 2014/0247047 A1 Sep. 4, 2014

Related U.S. Application Data

(63) Continuation of application No. 13/844,446, filed on Mar. 15, 2013, which is a continuation-in-part of application No. 13/623,759, filed on Sep. 20, 2012, now abandoned, which is a continuation of application (Continued)

(51) Int. Cl.
| | |
|---|---|
| *A61B 5/05* | (2006.01) |
| *G01R 33/48* | (2006.01) |
| *G01R 33/561* | (2006.01) |
| *A61B 5/055* | (2006.01) |
| *G01R 33/36* | (2006.01) |

(52) U.S. Cl.
CPC .............. *G01R 33/48* (2013.01); *G01R 33/561* (2013.01); *A61B 5/055* (2013.01); *G01R 33/36* (2013.01)

(58) Field of Classification Search
USPC ........... 600/410, 411, 419; 324/307, 309, 319
See application file for complete search history.

(56) References Cited

U.S. PATENT DOCUMENTS

| | | | |
|---|---|---|---|
| 3,792,346 A | 2/1974 | Gibby et al. | |
| 5,345,174 A | 9/1994 | Kimmich et al. | |
| 5,789,921 A | 8/1998 | Albert et al. | |
| 6,241,966 B1 | 6/2001 | Albert et al. | |
| 6,426,058 B1* | 7/2002 | Pines et al. ..................... | 424/9.3 |
| 6,453,188 B1* | 9/2002 | Ardenkjaer-Larsen et al. ............................ | 600/420 |
| 6,651,459 B2 | 11/2003 | Kalechofsky | |
| 7,053,611 B2 | 5/2006 | Freedman | |
| 7,199,584 B2* | 4/2007 | Meriles ........................ | 324/316 |

(Continued)

FOREIGN PATENT DOCUMENTS

| | | |
|---|---|---|
| RU | 2186405 C2 | 7/2002 |
| RU | 2377609 C2 | 12/2009 |

(Continued)

OTHER PUBLICATIONS

Yukalov, VI. Nuclear Spin Superradiance. eMagRes. (2002).*

(Continued)

*Primary Examiner* — Parikha Mehta
(74) *Attorney, Agent, or Firm* — Brian R. Pollack; Day Pitney LLP

(57) ABSTRACT

The present disclosure provides various methods and systems for performing magnetic resonance studies. In accordance with many embodiments, image or other information of interest is derived from super radiant pulses.

18 Claims, 11 Drawing Sheets

Related U.S. Application Data

No. PCT/US2012/030384, filed on Mar. 23, 2012, application No. 14/188,410, which is a continuation of application No. 13/844,446.

(60) Provisional application No. 61/466,500, filed on Mar. 23, 2011, provisional application No. 61/522,076, filed on Aug. 10, 2011, provisional application No. 61/667,283, filed on Jul. 2, 2012, provisional application No. 61/706,100, filed on Sep. 26, 2012, provisional application No. 61/706,102, filed on Sep. 26, 2012, provisional application No. 61/706,106, filed on Sep. 26, 2012, provisional application No. 61/882,430, filed on Sep. 25, 2013, provisional application No. 61/733,415, filed on Dec. 4, 2012.

(56) References Cited

U.S. PATENT DOCUMENTS

| | | |
|---|---|---|
| 7,372,274 B2 | 5/2008 | Ardenkjaer-Larsen et al. |
| 2006/0290350 A1 | 12/2006 | Hursan et al. |
| 2007/0249929 A1 | 10/2007 | Jeong et al. |
| 2010/0090693 A1 | 4/2010 | Wald et al. |
| 2010/0256477 A1 | 10/2010 | Harvey et al. |
| 2010/0327866 A1 | 12/2010 | Albu et al. |
| 2011/0101979 A1 | 5/2011 | Wiesinger et al. |
| 2011/0187366 A1 | 8/2011 | Grodzki |
| 2012/0095324 A1 | 4/2012 | Schmidt |
| 2012/0229136 A1 | 9/2012 | Stemmer |
| 2013/0154643 A1 | 6/2013 | Kalechofsky |
| 2013/0265048 A1 | 10/2013 | Kalechofsky |
| 2014/0247047 A1 | 9/2014 | Kalechofsky |
| 2014/0266197 A1 | 9/2014 | Kalechofsky |
| 2014/0285191 A1 | 9/2014 | Kalechofsky |
| 2014/0285192 A1 | 9/2014 | Kalechofsky |

FOREIGN PATENT DOCUMENTS

| | | |
|---|---|---|
| RU | 2386140 C2 | 4/2010 |
| RU | 2411528 C2 | 2/2011 |
| SU | 1702271 A1 | 12/1991 |
| WO | 9737239 A1 | 10/1997 |
| WO | 2007/002678 A2 | 1/2007 |
| WO | 2009018088 A2 | 2/2009 |
| WO | 2011018719 A1 | 2/2011 |

OTHER PUBLICATIONS

International Search Report in corresponding international application PT/US2012/030384, mailed on Jun. 28, 2012.

USPTO Non-Final Office Action issued in related U.S. Appl. No. 13/623,759, May 10, 2013.

USPTO Non-Final Office Action issued in related U.S. Appl. No. 13/763,967, May 14, 2013.

International Search Report dated Oct. 2, 2013 for PCT/US2013/049014, 2 pages.

Notification of Transmittal of International Search Report and Written Opinion dated Jul. 1, 2014, International Search Report dated Jul. 11, 2014, and Written Opinion dated Jul. 11, 2014 for PCT/US2014/026829, 6 pages.

Notification of Transmittal of International Search Report and Written Opinion dated Aug. 7, 2014, International Search Report dated Aug. 7, 2014, and Written Opinion dated Aug. 7, 2014 for PCT/US2014/028343, 6 pages.

International Search Report dated Sep. 25, 2014 for PCT/US2014/026862, 2 pages.

Notification of Transmittal of International Search Report and Written Opinion dated Sep. 25, 2014, International Search Report dated Sep. 25, 2014, and Written Opinion dated Sep. 25, 2014 for PCT/US2014/026862, 7 pages.

\* cited by examiner

Example – Field Map Of A z2 Shim On A Siemens MRI. The Gradient Is Very Steep Except Near The Center Of The Saddle Region Image Made Using SR Pulses.

Example – Simulation Of A Subject Inside A FEC Coil With SSR Volume Included Next To Him. The FEC Electonics Can Be Located Outside The MR Suit

TECHNIQUES, SYSTEMS AND MACHINE READABLE PROGRAMS FOR MAGNETIC RESONANCE

CROSS-REFERENCE TO RELATED APPLICATIONS

This application is a continuation of and claims the benefit of priority to U.S. patent application Ser. No. 13/844,446, filed Mar. 15, 2013, published as US2013/0265048 which in turn is a continuation-in-part of and claims the benefit of priority to U.S. patent application Ser. No. 13/623,759 filed Sep. 20, 2012, published as US2013/0253308, which in turn claims the benefit of priority of and is a continuation of International Patent Application No. PCT/US2012/30384, filed Mar. 23, 2012, published as WO 2012/129512, which in turn claims the benefit of priority to U.S. Provisional Patent Application Ser. No. 61/466,500, filed Mar. 23, 2011 and U.S. Provisional Patent Application Ser. No. 61/522,076, filed Aug. 10, 2011. This application is a continuation of and claims the benefit of priority to U.S. patent application Ser. No. 13/844,446, filed Mar. 15, 2013, published as US2013/0265048, which in turn claims the benefit of priority to U.S. Provisional Patent Application Ser. No. 61/667,283, filed Jul. 2, 2012, U.S. Provisional Patent Application Ser. No. 61/706,100, filed Sep. 26, 2012, U.S. Provisional Patent Application Ser. No. 61/706,102, filed Sep. 26, 2012, U.S. Provisional Patent Application Ser. No. 61/706,106, filed Sep. 26, 2012, and U.S. Provisional Patent Application Ser. No. 61/733,415, filed Dec. 4, 2012. This patent application claims the benefit of priority to U.S. Patent Application Ser. No. 61/882,430, filed Sep. 25, 2013. The disclosure of each of the aforementioned patent applications is incorporated by reference herein in its entirety for any purpose whatsoever.

BACKGROUND OF THE DISCLOSURE

1. Field of the Disclosure

The present disclosure relates to improved techniques, systems and machine readable programs for magnetic resonance imaging.

2. Description of Related Art

Traditionally NMR/MRI/MRS studies have always incorporated pulses of radiofrequency (rf) radiation. The role of the rf pulses is to excite the system under investigation into a temporary state of non equilibrium magnetization. As the system relaxes back to equilibrium it emits radiation which can then be used to form images and/or extract information of scientific or diagnostic value such as physical state of the system, quantity of a given molecule, diffusion coefficients, spectroscopic identification, etc. A variety of rf pulse sequences designed to extract information of one kind or another in this manner are well described in the literature. There is a continuing need in the MRI art for advances that can increase the speed of imaging, require less data storage and improve image quality. The present disclosure provides solutions for these problems.

SUMMARY OF THE DISCLOSURE

Advantages of the present disclosure will be set forth in and become apparent from the description that follows. Additional advantages of the disclosure will be realized and attained by the methods and systems particularly pointed out in the written description and claims hereof, as well as from the appended drawings.

To achieve these and other advantages and in accordance with the purpose of the disclosure, as embodied herein, in one embodiment, the disclosure provides a method of performing a magnetic resonance protocol. The method includes providing a magnetic resonance device including (i) a main magnet for providing a background magnetic field along a first direction, (ii) at least one radio-frequency coil, and (iii) at least one gradient coil that can be controlled to define at least one region of interest. The method further includes defining a region of interest, introducing a sample or subject to be studied into the region of interest and inducing electromagnetic feedback between the nuclear magnetization of at least one set of nuclei within the sample or subject and at least one nearby resonant coil to cause the vector direction of the nuclear magnetization of the at least one set of nuclei to rotate to a desired angle with respect to the first direction of the background magnetic field to generate at least one electromagnetic pulse of transverse magnetization $M_{XY}$. The method further includes detecting rf pulses from the sample or subject or with the at least one radio-frequency coil. The method further includes usage of a feedback enabled coil (FEC) and an additional Supplementary Spin Reservoir (SSR), described more fully below, as techniques for enabling feedback of nuclear magnetism to occur even under clinical MRI conditions where it normally would not.

In accordance with a further embodiment, a method for performing quantitative analysis of the amount of a molecule in a sample or subject or subject is provided. The method includes providing a magnetic resonance device including (i) a main magnet for providing a background magnetic field along a first direction, (ii) at least one radio-frequency coil, and (iii) at least one gradient coil that can be controlled to define at least one region of interest, introducing into the MR device at least one SSR containing a plurality of molecules, adjusting the circuitry of the resonant coil in order to induce electromagnetic feedback between the nuclear magnetization of at least one set of nuclei within the SSR and the at least one nearby resonant coil to cause the system to achieve a desired relationship between $\tau R$ and $T_2$, introducing RF pulses into the SSR so that the magnetization of at least one set of nuclei within the SSR is rotated to greater than ninety degrees, analyzing the SR pulse that results from step e to determine the peaktime and width of the SR pulse, introducing a sample or subject to be studied into the region of interest, (h) introducing RF pulses into the sample or subject and the SSR so as to so that the magnetization of at least one set of nuclei within the SSR is rotated to the same angle as earlier, (i) analyzing the SR pulse that results from step h) to determine the peaktime and width of the new SR pulse, (j) subtracting the pulse obtained in step f) from that in step h) to obtain quantitative information as to the amount of target molecule in the sample or subject.

In accordance with a further aspect, a first radio frequency coil is used to introduce RF pulses into the sample or subject, and a second radio frequency coil is used to induce electromagnetic feedback between the nuclear magnetization of the set of nuclei of interest and the second radio frequency coil. In another embodiment, the at least one radio frequency coil is used to introduce RF pulses into the sample or subject in a first selectable state, and the at least one radio frequency coil is also used to induce electromagnetic feedback between the nuclear magnetization of the set of nuclei of interest and the second radio frequency coil when in a second selectable state.

The disclosure also provides a method, including providing a magnetic resonance device including (i) a main magnet for providing a background magnetic field along a first direction, (ii) at least one radio-frequency coil, and (iii) at least one gradient coil that can be controlled to define a region of interest, introducing a sample or subject to be studied into the region of interest, introducing RF pulses into the sample or subject to energize nuclei in the sample or subject, inducing electromagnetic feedback between a first set of nuclei in the sample or subject and the at least one radio frequency coil to cause the vector direction of the nuclear magnetization of the first set of nuclei to rotate to a desired angle with respect to the first direction of the background magnetic field while substantially preventing electromagnetic feedback from being induced between a second set of nuclei in the sample or subject and the at least one resonant coil, activating a gradient magnetic field in the region of interest in order to destroy the magnetization associated with the first set of nuclei, deactivating gradient, employing RF pulses to rotate second set of nuclear magnetization to a desired angle, detecting a signal relating to the pulse of transverse magnetization, and processing the signal to form a data set relating to the presence of the second set of nuclei in the sample or subject.

If desired, the method can further include processing information obtained from a plurality of pulses of transverse magnetization to produce at least one of (i) an image, (ii) dynamic flow data, (iii) perfusion data, (iii) spectroscopic identity of chemical species, (iv) physiological data, or (v) metabolic data. If desired, the method can further include inducing electromagnetic feedback to cause the vector direction of the nuclear magnetization of the second set of nuclei to rotate to a desired angle with respect to the first direction of the background magnetic field, and stopping the electromagnetic feedback to permit the second set of nuclei to permit the pulse of transverse magnetization to propagate. Electromagnetic feedback can be induced at least in part by substantially eliminating the presence of a gradient magnetic field in the at least one region of interest. Electromagnetic feedback can be induced at least in part by selectively tuning the at least one radio frequency coil to a predetermined resonant frequency. The sample or subject to be studied can be an in-vivo sample or subject including fat and water, and further wherein a pulse of transverse magnetization can be detected with the at least one radio-frequency coil from protons in water, and further wherein substantially no transverse magnetization may be detected with the at least one radio-frequency coil from protons in fat.

A further method is also provided for performing a magnetic resonance protocol, including providing a magnetic resonance device including (i) a main magnet for providing a background magnetic field along a first direction, (ii) at least one radio-frequency (RF) coil, and (iii) at least one gradient coil that can be controlled to define at least one region of interest, introducing a sample or subject to be studied into the device, defining a region of interest from which to receive a SR pulse within the sample or subject by adjusting the magnetic field gradient in the region of interest to be substantially zero, introducing RF pulses into the sample or subject to energize nuclei in the sample or subject, inducing electromagnetic feedback between the nuclear magnetization of a first set of nuclei within the sample or subject and the RF coil to cause the vector direction of the nuclear magnetization of the first set of nuclei to rotate to a desired angle with respect to the first direction of the background magnetic field to generate at least one electromagnetic pulse of transverse magnetization MXY, wherein the vector direction of the nuclear magnetization of a second set of nuclei outside of the region of interest does not substantially change when the at least one electromagnetic pulse is generated, and detecting the pulse of transverse magnetization arising from the region of interest using an Rf coil.

If desired, the method can further include processing information obtained from one or more pulses of transverse magnetization to produce at least one of (i) an image, (ii) dynamic flow data, (iii) perfusion data, (iii) spectroscopic identity of chemical species, (iv) physiological data, or (v) metabolic data. Electromagnetic feedback can be induced at least in part by selectively tuning the resonant coil to a predetermined resonant frequency.

The disclosure further provides a method for performing magnetic resonance spectroscopic imaging, including providing a magnetic resonance device including (i) a main magnet for providing a background magnetic field along a first direction, (ii) at least one resonant feedback enabled coil, and (iii) at least one gradient coil that can be controlled to define at least one region of interest, introducing a sample or subject to be studied into the region of interest, carrying out MR pulse sequence protocols to produce at least one of (i) an image, (ii) dynamic flow data, (iii) perfusion data, (iii) spectroscopic identity of chemical species, (iv) physiological data, or (v) metabolic data, and adjusting the circuitry of the RF coil in order to induce electromagnetic feedback between the nuclear magnetization of at least one set of nuclei within the sample or subject and the at least one resonant feedback enabled coil to cause at least one of (i) the vector direction of the nuclear magnetization of the at least one set of nuclei within the sample or subject to rotate to a new desired angle with respect to the direction of the background magnetic field and (ii) the precessional frequency of at least one set of nuclei within the sample or subject to shift with respect to the precessional frequency of other nuclei in the sample or subject. It will be appreciated that all methods described herein have corresponding systems and machine readable programs as set forth herein, and can be expressed as such.

In some implementations, the method can further include processing information obtained from a plurality of pulses of transverse magnetization to produce at least one of (i) an image, (ii) dynamic flow data, (iii) perfusion data, (iii) spectroscopic identity of chemical species, (iv) physiological data, or (v) metabolic data. In some embodiments, the electromagnetic feedback can be induced at least in part by substantially eliminating the presence of a gradient magnetic field in the at least one region of interest. The region of interest can include, for example, at least one voxel, and the at least one gradient coil can be adapted and configured to apply a magnetic field gradient in at least one of three mutually orthogonal directions. The electromagnetic feedback can be induced at least in part by selectively tuning the resonant coil to a predetermined resonant frequency.

In further implementations, the method can further include applying a RF pulse to the sample or subject in order to at least partially invert the nuclear magnetization of the at least one set of nuclei prior to the inducing step. In some embodiments, the magnetization vector of the at least one set of nuclei can be directed substantially entirely anti-parallel to the first direction of the background magnetic field. The background magnetic field can be, for example, about 1.0 Tesla, about 1.5 Tesla, about 2.0 Tesla, about 2.5 Tesla, about 3.0 Tesla, about 4.0 Tesla, about 5.0 Tesla, about 6.0 Tesla, about 7.0 Tesla, about 8.0 Tesla, about 9.0 Tesla, about 10.0 Tesla or greater or less, in any desired increment of 0.1 Tesla. The vector direction of the nuclear magnetization of the at least one set of nuclei can be permitted to fully align with the first direction of the background magnetic field when the pulse is generated. If desired, the vector direction of the nuclear magnetization of the at least one set of nuclei can be permitted to partially align with the first direction of the background magnetic field when the pulse is generated. If desired, the method can further include generating a plurality of pulses of transverse magnetization from the at least one set of nuclei by permitting the vector direction of the nuclear magnetization of the at least one set of nuclei to progressively and discretely approach full alignment with the first direction of the background magnetic field with each succeeding pulse of transverse magnetization.

In some implementations, the inducing step can include inducing electromagnetic feedback between the nuclear magnetization of a plurality of sets of nuclei in at least two discrete, separated physical locations within the object and at least one nearby resonant coil to cause the vector direction of the nuclear magnetizations of each set of nuclei to rotate to a desired angle with respect to the first direction of the background magnetic field to generate the at least one electromagnetic pulse of transverse magnetization.

In some implementations, at least one of the at least one radio frequency coil and the at least one gradient coil is a local coil. Moreover, at least one of the at least one radio frequency coil and the at least one gradient coil can be integrated into the magnetic resonance system. If desired, the at least one radio frequency coil can be a whole body coil, and can be used at background fields in excess of 3.0 Tesla. If desired, the at least one radio frequency coil can be a whole body phased array transmit/receive coil system having a plurality of coils that can selectively transmit and receive rf pulses of transverse magnetization. Moreover, the at least one radio frequency coil can be a local phased array transmit/receive coil system having a plurality of coils that can selectively transmit and receive rf pulses of transverse magnetization. If desired, the at least one radio frequency coil can further include a plurality of local gradient coils for locally controlling the gradient magnetic field. If desired, the at least one gradient field coil can include a plurality of gradient field coils integrated into the magnetic resonance system, even if local gradient field coils are provided.

In further implementations, a coil designed to amplify feedback can be employed. The coil can additionally and optionally be made to permit manipulation of the phase of the feedback field. This coil is referred to in this document as a Feedback Enabled Coil (FEC).

In further implementations, the method includes inserting a volume containing a plurality of molecules in the field of view (FOV) of either the resonant coil or the FEC. This volume, termed the Supplementary Spin Reservoir (SSR), permits the production of feedback even under relatively low conditions of clinical MRI scanners. In addition, by selecting the molecule (or molecules) inside the SSR, the feedback field can be made to resonate at a desired frequency or set of frequencies.

In accordance with further aspects, the disclosure provides systems for performing a magnetic resonance protocol. The system can include a magnetic resonance device including (i) a main magnet for providing a background magnetic field along a first direction, (ii) at least one radio-frequency coil, and (iii) at least one gradient coil that can be controlled to define at least one region of interest. The system can further include means for defining a region of interest, means for introducing a sample or subject to be studied into the region of interest and means for inducing electromagnetic feedback between the nuclear magnetization of at least one set of nuclei within the sample or subject and at least one nearby resonant coil to cause the vector direction of the nuclear magnetization of the at least one set of nuclei to rotate to a desired angle with respect to the first direction of the background magnetic field to generate at least one electromagnetic pulse of transverse magnetization $M_{xy}$. The method can still further include means for detecting the pulse of transverse magnetization with the at least one radio-frequency coil.

In some implementations the system can further include means for processing information obtained from a plurality of pulses of transverse magnetization to produce at least one of (i) an image, (ii) dynamic flow data, (iii) perfusion data, (iii) spectroscopic identity of chemical species, (iv) physiological data, and (v) metabolic data. If desired, electromagnetic feedback can be induced at least in part by substantially eliminating the presence of a gradient magnetic field in the at least one region of interest by controlling the at least one gradient coil. The region of interest can include at least one voxel, and the at least one gradient coil is adapted and configured to apply a magnetic field gradient in at least one of three mutually orthogonal directions. Electromagnetic feedback can be induced at least in part by selectively tuning the at least one rf coil to a predetermined resonant frequency. The system can selectively and controllably apply a RF pulse to the sample or subject in order to at least partially invert the nuclear magnetization of the at least one set of nuclei prior to the inducing step. In some embodiments, the system can be adapted to direct the magnetization vector of the at least one set of nuclei substantially entirely anti-parallel to the first direction of the background magnetic field. The background magnetic field can be, for example, about 1.0 Tesla, about 1.5 Tesla, about 2.0 Tesla, about 2.5 Tesla, about 3.0 Tesla, about 40.0 Tesla, about 5.0 Tesla, about 6.0 Tesla, about 7.0 Tesla, about 8.0 Tesla, about 9.0 Tesla, about 10.0 Tesla or greater or less, in any desired increment of 0.1 Tesla. The system can be adapted to permit the vector direction of the nuclear magnetization of the at least one set of nuclei to fully align with the first direction of the background magnetic field when the pulse is generated. In some embodiments, the system can be adapted to permit the vector direction of the nuclear magnetization of the at least one set of nuclei to partially align with the first direction of the background magnetic field when the pulse is generated. If desired, the system can be further adapted to selectively and controllably generate a plurality of pulses of transverse magnetization at different times from the at least one set of nuclei by permitting the vector direction of the nuclear magnetization of the at least one set of nuclei to progressively and discretely approach full alignment with the first direction of the background magnetic field with each succeeding pulse of transverse magnetization.

In some implementations, the system can be adapted to induce electromagnetic feedback between the nuclear magnetization of a plurality of sets of nuclei in at least two discrete, separated physical locations within the object and at least one nearby resonant coil to cause the vector direction of the nuclear magnetizations of each set of nuclei to rotate to a desired angle with respect to the first direction of the background magnetic field to generate the at least one electromagnetic pulse of transverse magnetization. In some embodiments, at least one of the at least one radio frequency coil and the at least one gradient coil can be a local coil. At least one of the at least one radio frequency coil and the at least one gradient coil can be integrated into the magnetic resonance system. The at least one radio frequency coil can be a whole body coil. The at least one radio frequency coil can be a whole body phased array transmit/receive coil system having a plurality of coils that can selectively transmit and receive rf pulses of transverse magnetization. The at least one radio frequency coil can be a local phased array transmit/receive coil system having a plurality of coils that can selectively transmit and receive rf pulses of transverse magnetization. At least one radio frequency coil can further include a plurality of local gradient coils for locally controlling the gradient magnetic field. The at least one gradient field coil can include a plurality of gradient field coils integrated into the magnetic resonance system, as well as one or more local gradient coils, if desired.

The disclosure further provides processor-readable computer programs stored on a tangible non-transient medium for operating a magnetic resonance protocol on a magnetic resonance device including, for example, (i) a main magnet for providing a background magnetic field along a first direction, (ii) at least one radio-frequency coil, and (iii) at least one gradient coil that can be controlled to define at least one region of interest. The program can include instructions to facilitate definition of a region of interest, instructions for inducing electromagnetic feedback between the nuclear magnetization of at least one set of nuclei within the sample or subject and at least one nearby resonant coil to cause the vector direction of the nuclear magnetization of the at least one set of nuclei to rotate to a desired angle with respect to the first direction of the background magnetic field to generate at least one electromagnetic pulse of transverse magnetization $M_{xy}$, and instructions to facilitate processing signals received arising from the pulse of transverse magnetization with the at least one radio-frequency coil.

The computer program can further include instructions for processing information obtained from a plurality of pulses of transverse magnetization to produce at least one of (i) an image, (ii) dynamic flow data, (iii) perfusion data, (iii) spectroscopic identity of chemical species, (iv) physiological data, and (v) metabolic data. The program can further include instructions to induce electromagnetic feedback by substantially eliminating the presence of a gradient magnetic field in the at least one region of interest by controlling the at least one gradient coil. The region of interest can include at least one voxel, and the program can include instructions to cause the at least one gradient coil to apply a magnetic field gradient in at least one of three mutually orthogonal directions. The program can include instructions to induce electromagnetic feedback at least in part by selectively tuning the at least one rf coil to a predetermined resonant frequency. The program can similarly include instructions to cause the system to selectively and controllably apply a RF pulse to the sample or subject in order to at least partially invert the nuclear magnetization of the at least one set of nuclei prior to inducing the electromagnetic feedback.

In some implementations, the computer program can include instructions to cause the magnetic resonance system to direct the magnetization vector of the at least one set of nuclei substantially entirely anti-parallel to the first direction of the background magnetic field. Similarly, the computer program can include instructions to cause the magnetic resonance system to permit the vector direction of the nuclear magnetization of the at least one set of nuclei to fully align with the first direction of the background magnetic field when the pulse is generated. The computer program can include instructions to cause the magnetic resonance system to permit the vector direction of the nuclear magnetization of the at least one set of nuclei to partially align with the first direction of the background magnetic field when the pulse is generated.

In further implementations, the computer program can further include instructions to cause the magnetic resonance system to selectively and controllably generate a plurality of pulses of transverse magnetization at different times from the at least one set of nuclei by permitting the vector direction of the nuclear magnetization of the at least one set of nuclei to progressively and discretely approach full alignment with the first direction of the background magnetic field with each succeeding pulse of transverse magnetization. The computer program can similarly include instructions to cause the magnetic resonance system to induce electromagnetic feedback between the nuclear magnetization of a plurality of sets of nuclei in at least two discrete, separated physical locations within the object and at least one nearby resonant coil to cause the vector direction of the nuclear magnetizations of each set of nuclei to rotate to a desired angle with respect to the first direction of the background magnetic field to generate the at least one electromagnetic pulse of transverse magnetization.

In some implementations, the computer program can include instructions to cause the magnetic resonance system to operate at least one radio frequency coil and at least one gradient coil that is a local coil. The computer program can include instructions to cause the magnetic resonance system to operate at least one radio frequency coil and at least one gradient coil that is integrated into the magnetic resonance system. The computer program can include instructions to operate a radio frequency coil that is a whole body phased array transmit/receive coil system having a plurality of coils that can selectively transmit and receive rf pulses of transverse magnetization. If desired, the computer program can include instructions to operate a radio frequency coil that is a local phased array transmit/receive coil system having a plurality of coils that can selectively transmit and receive rf pulses of transverse magnetization. The computer program can similarly include instructions to operate at least one radio frequency coil that further includes a plurality of local gradient coils for locally controlling the gradient magnetic field.

It is to be understood that the foregoing general description and the following detailed description are exemplary and are intended to provide further explanation of the disclosed embodiments. The accompanying drawings, which are incorporated in and constitute part of this specification, are included to illustrate and provide a further understanding of the disclosed methods and systems. Together with the description, the drawings serve to explain principles of the disclosure.

DETAILED DESCRIPTION

Figure 1:
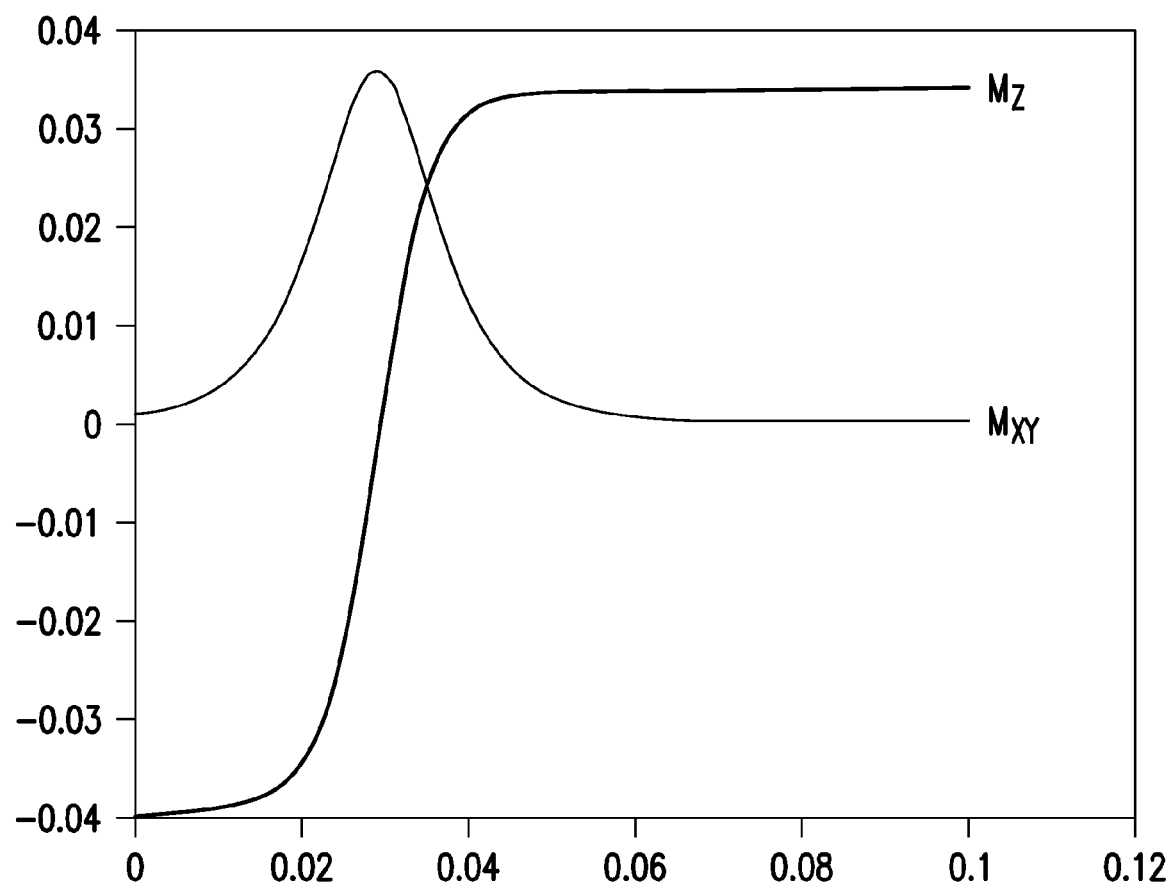
FIG. 1 illustrates a simulated SR pulse resulting from inverting the magnetization of a single ensemble of nuclei in accordance with the disclosure.

Reference will now be made in detail to the present preferred embodiments of the disclosure, examples of which are illustrated in the accompanying drawings. The methods and corresponding steps of the disclosed embodiments will be described in conjunction with the detailed description of the system.

Mathematical Description of Superradiance:

The equation of motion of the nuclear magnetization in an MR study in a homogenous field is:

$$\frac{d\vec{M}}{dt} = \gamma \vec{M} \times \vec{B} - \vec{R}(\vec{M} - \vec{M}_o) \quad [1]$$

wherein M is the nuclear magnetization, B are the magnetic fields, and R is the relaxation matrix.

Transforming to a reference frame rotating with the rf field at frequency ω with:

$$M_z = m_z \quad M_\pm = e^{\pm j\omega t} m_\pm$$

$$B_\pm = B_{1\pm} e^{\pm j\omega t} \quad [2]$$

gives the Bloch equations in the rotating frame of the rf field:

$$\frac{dm_z}{dt} = j\gamma(m_+ B_{1-} - m_- B_{1+})/2 - (m_z - M_o)/T_1 \quad [3]$$

$$\frac{dm_\pm}{dt} = \mp j(\omega + \gamma B_z)m_\pm \pm j\gamma m_z B_{1\pm}/T_2$$

Wherein $T_1$ is the constant of exponential relaxation of the longitudinal (z) magnetization and $T_2$ is the exponential constant of relaxation of the transverse magnetization.

Defining $m_\pm = m e^{\pm j\phi}$ will allow a separation of the Bloch equations into magnitude and phase for the transverse magnetization.

$$\frac{dm_\pm}{dt} = \frac{de^{\pm j\phi}m}{dt} = \pm jme^{\pm j\phi}\frac{d\phi}{dt} + e^{\pm j\phi}\frac{dm}{dt} = \quad [4]$$

$$\mp j(\omega + \gamma B_z)e^{\pm j\phi}m \pm j\gamma m_z B_{1\pm} - e^{\pm j\phi}m/T_2 \pm j\frac{d\phi}{dt} + \frac{dm}{mdt} =$$

$$\mp j(\omega + \gamma B_z) + j\gamma m_z \frac{B_{1\pm}}{m e^{\pm j\phi}} - 1/T_2$$

$$\frac{d\phi}{dt} = -(\omega + \gamma B_z) + \frac{\gamma m_z}{m}\text{Re}\{B_{1\pm}e^{\mp j\phi}\}$$

$$\frac{d\phi}{dt} = \mp \frac{\gamma m_z}{m}\text{Im}\{B_{1\pm}e^{\mp j\phi}\} - 1/T_2$$

Wherein Re and Im refer to the real and imaginary parts.

Adding Feedback:

Now feedback may be added, so that:

$$B_{1\pm} = \beta e^{\pm j\alpha}m_\pm = \beta m e^{\pm j(\alpha+\phi)} \quad [5]$$

then from equations [3,4]:

$$\frac{dm_z}{dt} = \gamma B m^2 \sin\alpha - (m_z - M_o)/T_1 \quad [6]$$

$$\frac{d\phi}{dt} = -(\omega + \gamma B_z) + \gamma \beta m_z \cos\alpha$$

$$\frac{dm}{mdt} = \gamma \beta m_z \sin\alpha - 1/T_2$$

Note that the second equation with cos α=0, suggests that the rf field frequency is locked to $B_z$. To see this, solve for φ.

$$\phi = -(\omega + \gamma B_z)t + \gamma B\cos\alpha \int m_z dt \quad [7]$$

if $$\cos\alpha = 0,$$

$$\phi = -(\omega + \gamma B_z)t$$

∴

$$M_\pm = m e^{\pm j\omega t} e^{\pm j\phi}$$

$$= m e^{\mp j\gamma B_z t}$$

$$B_\pm = \left\{\begin{array}{c}\pm\\\mp\end{array}\right\} jm\beta e^{\mp j\gamma B_z t}$$

with the ± signs in the bracket corresponding to sin α=±1 and ω=−γ$B_z$. The ±j factor for $B_\pm$ indicates that the rf field must be phase shifted ±90° with respect to the magnetization.

If we write γβ$m_z$ sin α=$\tau_R$ where $\tau_R$ is known as the "superradiant" time it is clear from Equation 6 that where dm/dt=0 is where $\tau_R$=$T_2$. This also defines the ambient conditions for superradiance to occur; ie where $\tau_R$≤$T_2$ the dynamics of the magnetization are dominated by superradiance rather than "ordinary" relaxation.

Differential Equation and Solution;

A differential equation may be developed from Equation [6]. First make a substitution for d$m_z$/dt to obtain:

$$\frac{d}{dt}\frac{dm}{mdt} = -\gamma\beta\sin\alpha(\gamma\beta m^2\sin\alpha - (m_z - M_o)/T_1)$$

A solution may be obtained for a sufficiently long $T_1$, thus $$\frac{d}{dt}\frac{dm}{mdt} = -(\gamma\beta\sin\alpha m)^2 \quad [7]$$

Solution for m is given by $\mu$sech($\mu\gamma\beta$ sin α(t−$t_o$)) where μ and $t_o$ are constants to be determined. Verify:

$$\frac{d}{dt}\frac{d\mu\text{sech}(\gamma\beta\mu\sin\alpha(t-t_o))}{\mu\text{sech}(\gamma\beta\mu\sin\alpha(t-t_o))dt} =$$

$$\frac{d}{dt}\frac{[-\gamma\beta\sin\alpha\mu^2\tanh(\gamma\beta\mu\sin\alpha(t-t_o))\text{sech}(\gamma\beta\mu\sin\alpha(t-t_o))]}{\mu\text{sech}(\gamma\beta\mu\sin\alpha(t-t_o))} =$$

$$\frac{d[-\gamma\beta\sin\alpha\mu\tanh(\gamma\beta\mu\sin\alpha(t-t_o))]}{dt} =$$

$$-(\gamma\beta\mu\sin\alpha)^2\text{sech}^2(\gamma\beta\mu\sin\alpha(t-t_o)) = -(\gamma\beta\sin\alpha m)^2$$

Solution for $m_z$ may be developed from the third equation in eq.[6].

$$\frac{dm}{mdt} = -\gamma\beta m_z\sin\alpha - 1/T_2$$

$$\frac{dm}{mdt} = \frac{-\gamma\beta\sin\alpha\mu\mu\tanh(\gamma\beta\mu\sin\alpha(t-t_o))\text{sech}(\gamma\beta\mu\sin\alpha(t-t_o))}{\mu\text{sech}(\gamma\beta\mu\sin\alpha(t-t_o))} =$$

$$-\gamma\beta\mu\sin\alpha\tanh(\gamma\beta\mu\sin\alpha(t-t_o)) = -\gamma\beta\sin\alpha m_z - 1/T_2$$

$$m_z = \mu\tanh(\gamma\beta\mu\sin\alpha(t-t_o)) - 1/\gamma\beta\sin\alpha T_2$$

At time, t=o, we have the following $$m_z(0) = -\mu \tan h(\gamma\beta\mu \sin \alpha t_o) - 1/\gamma\beta \sin \alpha T_2$$

$$m(0) = \mu \text{sech}(\gamma\beta\mu \sin \alpha t_o) \quad [8]$$

Since the total magnetization at t=o is equal to $M_o$, then $$M_o^2 = \mu^2 \text{sech}^2(\gamma\beta\mu\sin\alpha t_o) + \mu^2 \tanh^2(\gamma\beta\mu\sin\alpha t_o) +$$
$$2\mu\tanh(\gamma\beta\mu\sin\alpha t_o)/\gamma\beta\sin\alpha T_2 + (1/\gamma\beta\sin\alpha T_2)^2$$
$$M_o^2 = \mu^2 + 2\mu\tanh(\gamma\beta\mu\sin\alpha t_o)/\gamma\beta\sin\alpha T_2 + (1/\gamma\beta\sin\alpha T_2)^2$$
$$\left[1 - \left(\frac{\mu}{M_o}\right)^2 - \left(\frac{1}{\gamma\beta M_o \sin\alpha T_2}\right)^2\right] \frac{M_o}{2\mu} \gamma\beta M_o \sin\alpha T_2 = \tanh(\gamma\beta\mu\sin\alpha t_o)$$

Thus $\mu$ and $t_o$ may be dependent on each other. Using the expression for $m_z(o)$ from eq.[8] gives $$\left[1 - \left(\frac{\mu}{M_o}\right)^2 - \left(\frac{1}{\gamma\beta M_o \sin\alpha T_2}\right)^2\right] \gamma\beta M_o \sin\alpha T_2 = \quad [9]$$
$$-2\left(\frac{m_z(0)}{M_o} + \frac{1}{\gamma\beta M_o \sin\alpha T_2}\right)$$
$$\gamma\beta M_o \sin\alpha T_2 \left[\left(\frac{\mu}{M_o}\right)^2 - 1\right] = \frac{2m_z(0)}{M_o} + \frac{1}{\gamma\beta M_o \sin\alpha T_2}$$
$$\left(\frac{\mu}{M_o}\right)^2 = 1 + \frac{1}{\gamma\beta M_o \sin\alpha T_2}\left[\frac{2m_z(0)}{M_o} + \frac{1}{\gamma\beta M_o \sin\alpha T_2}\right]$$

To determine $t_o$ we can use the expression for m(o) from eq.[8] to give $$t_o = \frac{1}{\gamma\beta\mu|\sin\alpha|} \text{sech}^{-1}\left(\frac{m(o)}{\mu}\right) \quad [10]$$

where $$\text{sech}^{-1}(x) = \ln\left[\frac{1 + \sqrt{1-x^2}}{x}\right] \quad [11]$$

for
$0 < x \leq 1$

Let the brackets with the plus-minus sign, $\{\pm\}$ define sgn(sin $\alpha$). Also define $$\tau_R \equiv 1/\gamma\beta M_o |\sin\alpha| \quad [12]$$

Thus $$\mu = M_o \sqrt{1\{\pm\}\frac{\tau_R}{T_2}\left[\frac{2m_z(0)}{M_o}\{\pm\}\frac{\tau_R}{T_2}\right]} \equiv M_o \frac{\tau_R}{\tau}$$

and thus $$\frac{1}{\tau} = \frac{1}{\tau_R}\sqrt{1\{\pm\}\frac{\tau_R}{T_2}\left[\frac{2m_z(0)}{M_o}\{\pm\}\frac{\tau_R}{T_2}\right]} \quad [13]$$

Therefore $$m_z(t) = \{\pm\}M_o[(\tau_R/\tau)\tanh((t-t_o)/\tau) - \tau_R/T_2] \quad [14]$$
$$m(t) = M_o(\tau_R/\tau)\text{sech}((t-t_o)/\tau)$$

with $t_o$ determined by m(o) or by $m_z(o)$ as $$m_z(0) = \{\pm\}M_o[(\tau_R/\tau)\tanh((-t_o)/\tau) - \tau_R/T_2]$$

$$\left[\frac{\tau_R}{T_2}\{\pm\}\frac{m_z(0)}{M_o}\right]\frac{\tau}{\tau_R} = -\tanh(t_o/\tau)$$

$$= \frac{1 - e^{2t_o/\tau}}{1 + e^{2t_o/\tau}}$$

$$e^{2t_o/\tau} = \frac{1 - \left[\frac{\tau_R}{T_2}\{\pm\}\frac{m_z(0)}{M_o}\right]\frac{\tau}{\tau_R}}{1 + \left[\frac{\tau_R}{T_2}\{\pm\}\frac{m_z(0)}{M_o}\right]\frac{\tau}{\tau_R}}$$

$$t_o = \frac{\tau}{2}\ln\left[\frac{1 - \left[\frac{\tau_R}{T_2}\{\pm\}\frac{m_z(0)}{M_o}\right]\frac{\tau}{\tau_R}}{1 + \left[\frac{\tau_R}{T_2}\{\pm\}\frac{m_z(0)}{M_o}\right]\frac{\tau}{\tau_R}}\right] \quad [15]$$

$$t_o = \tau\text{sech}^{-1}\left(\frac{\tau}{\tau_R}\frac{m(0)}{M_o}\right) \quad [16]$$

The phase of the transverse magnetization is given by $$\phi(t) + \omega t = -\gamma B_z t + \gamma\beta\cos\alpha \int m_z dt \quad [17]$$

$$\phi(t) + \omega t =$$
$$-\gamma B_z t\{\pm\}M_o \gamma\beta\cos\alpha \int [(\tau_R/\tau)\tanh((t-t_o)/\tau) - \tau_R/T_2]dt$$

$$\phi(t) + \omega t = -\gamma B_z t \{\pm\}\frac{\cos\alpha}{|\sin\alpha|}[\ln\cosh((t-t_o)/\tau) - t/T_2 + C]$$

$$\phi(0) = \{\pm\}\frac{\cos\alpha}{|\sin\alpha|}[\ln\cosh(t_o/\tau) + C]$$
$$= 0$$

$$C = -\ln\cosh(t_o/\tau)$$

$$\phi(t) + \omega t = -\gamma B_z t\{\pm\}\frac{\cos\alpha}{|\sin\alpha|}\left[\ln\frac{\cosh((t-t_o)/\tau)}{\cosh(t_o/\tau)} - t/T_2\right]$$

The frequency of the magnetization is given by the derivative.

$$\omega_o \equiv \frac{d(\phi(t) + \omega t)}{dt} = -\gamma B_z\{\pm\}\frac{\cos\alpha}{|\sin\alpha|}[\tanh((t-t_o)/\tau)/\tau - 1/T_2] \quad [18]$$

Thus the frequency can change if the phase is not set correctly.

Summary

Under SR conditions ($\tau_R \leq T_2$) the equation of motion of the magnetization for the longitudinal and transverse nuclear magnetizations are:

$$m_z(t) = \{\pm\}M_o[(\tau_R/\tau)\tan h((t-t_o)/\tau) - \tau_R/T_2]$$
$$m(t) = M_o(\tau_R/\tau)\text{sech}((t-t_o)/\tau)$$

This produces a pulse of magnetization which peaks at time $t_o$ (FIG. 1):

$$t_o = \frac{\tau}{2}\ln\left[\frac{\frac{\tau_R}{\tau} - \frac{\tau_R}{T_2}\{\mp\}\frac{m_z(0)}{M_o}}{\frac{\tau_R}{\tau} + \frac{\tau_R}{T_2}\{\pm\}\frac{m_z(0)}{M_o}}\right] \quad [19]$$

$$= \tau\text{sech}^{-1}\left[\frac{\tau}{\tau_R}\frac{m(0)}{M_o}\right]$$

The phase of the transverse magnetization $$\omega_o = -\gamma B_z \{\pm\} \frac{\cos\alpha}{|\sin\alpha|} [\tanh((t-t_o)/\tau)/\tau - 1/T_2] \quad [20]$$

As $T_2 \to \infty$, $m_z(t) = \{\pm\} M_o \tanh((t-t_o)/\tau_R)$ $m(t) = M_o \text{sech}((t-t_o)/\tau_R)$ $$t_o = \frac{\tau}{2} \ln \left[ \frac{1\{\mp\}\frac{m_z(0)}{M_o}}{1\{\pm\}\frac{m_z(0)}{M_o}} \right]$$

$$= \tau_R \text{sech}^{-1} \left[ \frac{m(0)}{M_o} \right]$$

$$\omega_o = -\gamma B_z \{\pm\} \frac{\cos\alpha}{|\sin\alpha|} \frac{\tanh((t-t_o)/\tau_R)}{\tau_R}$$

Implications of the Superradiant State Equations of Motion:

Under appropriate conditions, the nuclear magnetism from one or more molecules in a sample or subject contained in one or more resonant coils can be made to feedback upon itself. Under such conditions we describe these molecule(s) as being in the "superradiant (SR) condition". The SR condition is defined as being where $\tau_R \leq T_2$. Clinical MR machines cannot normally produce the conditions necessary to produce $\tau_R \leq T_2$.

This disclosure teaches, in addition to other teachings, methods and systems for achieving the SR state even for low concentrations of molecules in otherwise clinical conditions. These teachings include: use of a feedback enabled coil (FEC) so that the active Q of one or more resonant coils of the MR machine can be made very high. In addition we teach the use of an additional volume, termed the Supplementary Spin Reservoir (SSR) which is inserted into the field of the MR device to ensure that one or more molecules in the MR device are in the SR condition.

Applicant has discovered methods of producing SR conditions in a localized volume in space. In a preferred embodiment, this is done by turning off/on, increasing/decreasing or changing in sign a local magnetic field gradient or gradients. Other embodiments for this include manipulating the probe Q (e.g., by detuning the coil selectively), frequency, and/or changing the parameters of the ambient magnetic field.

In the case where the gradient is sufficiently large such that $\tau_R \leq T_2^*$ (where $T_2^*$ represents the time it takes for any Mxy to dephase due to the action of the gradient) SR conditions are destroyed. In such an instance any longitudinal nuclear magnetization Mz remains "locked in" and undisturbed on time scales $t \ll T_1$. However the Mz is also unobservable as only Mxy can be detected in an MR study.

If the gradient is lowered such that $\tau_R \leq T_2$ SR conditions are re established. Applicant has discovered that the transition from SR to non SR conditions (ie where "normal" MR dynamics prevail) can be quite sharp, allowing the criteria for pulse production to be carefully controlled. By suppressing the gradient in a given region of space, an SR pulse can be produced that originates from a predefined spatial location. It can therefore be assigned a definite spatial value which is essential to creating a resolved image.

Traditionally SR conditions have been suppressed by using a gradient or gradients that are temporally structures—that is, that turn on/off in time. This suppresses or permits SR conditions in the entire volume located within the field of the resonant coil. Applicant has discovered that gradients can be spatially structured to allow SR conditions to exist in one part of a volume and suppressed in others. By careful manipulation of the nearby current coils the gradient can be made to be zero or very low—sufficiently low to permit SR conditions—in one voxel or other region of interest (e.g., comprising multiple voxels) while remaining large enough to deter SR conditions in the remaining fraction of the volume. By detecting the pulse resulting from SR conditions inside that one voxel its spatial location and spin content can be determined; the region of zero gradient can then be moved to produce signal from other voxels so as to produce sufficient information to construct an image. This can be done sequentially or in parallel to speed image production.

When the gradient field is suppressed in a local voxel such that the total gradient=o or is very low, an SR pulse can propagate. This causes any local Mz to rotate into the transverse plane and produce Mxy. Mxy is processing at the Larmor frequency and hence can be detected by the MR pick up coils. Local conditions can be adjusted—as a non exclusive example, by turning on/off a local gradient—so as to nutate only part of the local Mz into the xy plane. In this manner additional Mz is available to produce pulses at a later time should that be desirable. Or all of the local Mz can be used up in a single pulse. The spatial identity of the pulse can be determined in a number of manners. As a non exclusive example, this can be done by associating the zero point of the local gradient with a definite point or points in x,y,z. For example, the gradient field can be set to about zero for individual voxels spaced from one another in order to speed data acquisition by engaging in parallel data collection.

Local voxel or voxels of zero or very low gradient field can be produced and moved about in space by adjusting currents in nearby shim coils that are typically part of any MR imaging system. Thus an entire image can be built by manipulating the shim coils. Multiple voxels can be produced contemporaneously for example by causing the shim coils to have a time dependent current $I_o \cos(wt)$ rather than a static current $I_o$. By adjusting the current frequency in various shims multiple local voxels of zero or low gradient can be produced either permanently or temporarily as desired. If desired, a local coil can be provided surrounding or adjacent to a particular body part (e.g., a head/shoulder coil for neurovascular imaging, a back coil, knee coil, breast coil, etc.) that includes the capability to receive $M_{XY}$ pulses and that can optionally apply rf pulses and/or gradient fields to provide a further means for control of the local gradient field in the region of interest.

Because Mxy is only produced in a region of low or zero gradient, motion artifacts that plague traditional MR imaging can be reduced. Motion artifacts are produced when spins move in the high gradient fields used to produce images in traditional MR. As the spins move in the gradient they lose phase information which leads to image blurring. Producing pulses only in the region of low or zero gradient can be expected to suppress this phenomenon. Also, SR pulses from are inherently phase randomized so there cannot be build up of phase errors as the image is produced voxel by voxel.

Applicant has further discovered that the phase of any Mx converted under SR conditions from local Mz to Mxy can be distinguished from the phase of spins outside the local voxel. This allows the use of phase locked loops or similar methods to amplify the Mxy signal arising from spins in the local voxel of interest.

Occasionally it is desirable to extract local $T_2$ information while producing an MR image or carrying out other kinds of MR studies. $T_2$ mapping can provide contrast between different types of tissue in particular between spins in solid dense matter such as bone and that in surrounding tissue.

Applicant has discovered that $T_2$ contrast can be provided using the proposed technique. As a non exclusive example, this can be done by adjusting the Q of the resonant coil used to nutate any Mz into Mxy. Assuming a low or zero gradient, by increasing Q, the time for an SR pulse to propagate can be made faster than local $T_2$. Conversely, lowering Q can cause $T_2$ to be faster than the time required to produce an RD or SR pulse. In this circumstance no pulse can propagate. Thus regions of different $T_2$'s can be distinguished by controlling the local field gradient and adjusting the Q of the pick up coil.

The above described techniques can all be used in conjunction with standard imaging methodologies. For example, slice selective frequency encoding can be used to derive 2D information, with the above technique providing third dimensional information.

Exemplary MRI Scanner Systemization

Figure 2:
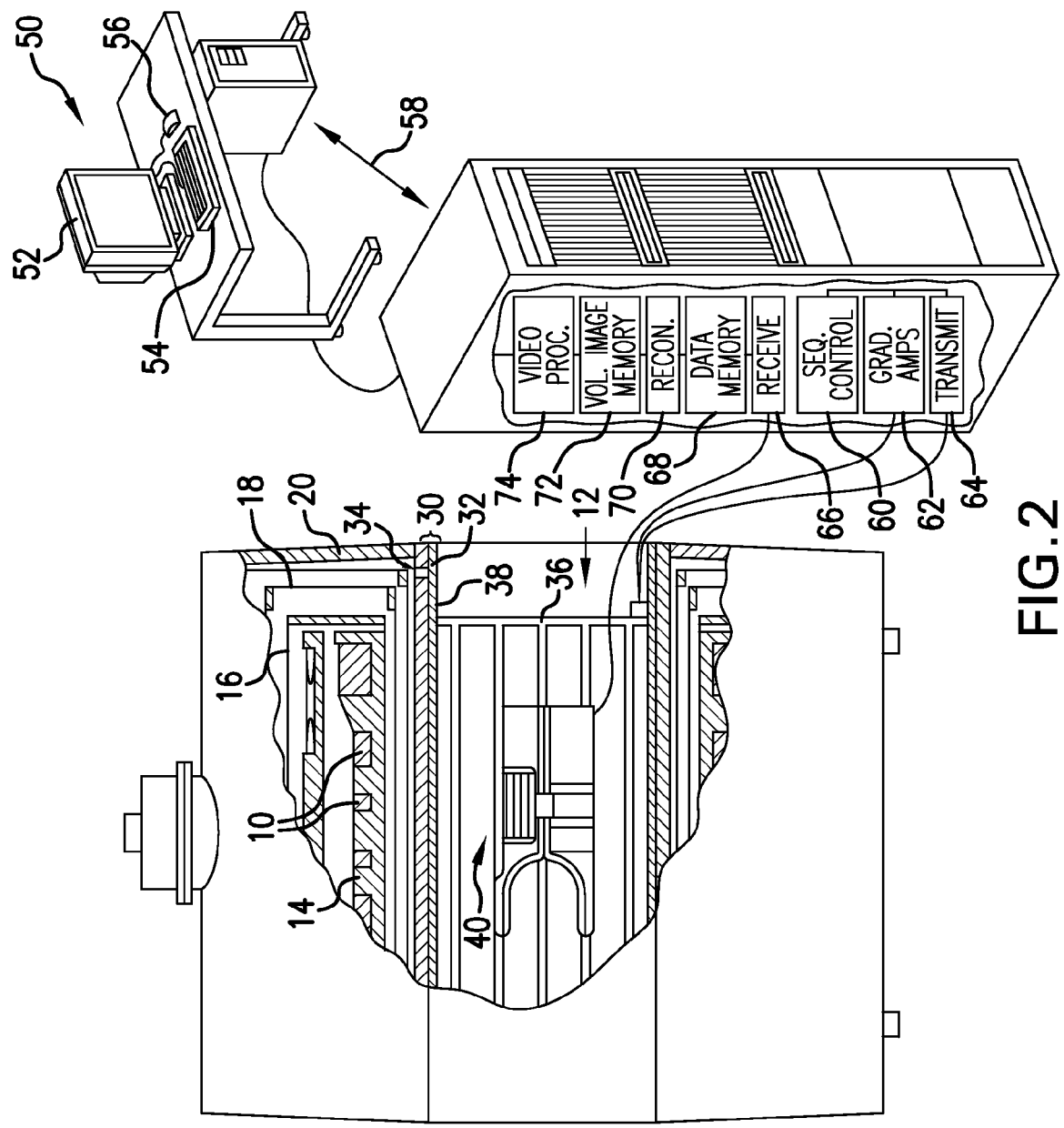
FIG. 2 depicts an exemplary magnetic resonance system in accordance with the disclosure.

An exemplary magnetic resonance system is depicted in FIG. 2, and includes a plurality of primary magnetic coils 10 that generate a uniform, temporally constant magnetic field $B_o$ along a longitudinal or z-axis of a central bore 12 of the device. In a preferred superconducting embodiment, the primary magnet coils are supported by a former 14 and received in a toroidal helium vessel or can 16. The vessel is filled with helium to maintain the primary magnet coils at superconducting temperatures. The can is surrounded by a series of cold shields 18 which are supported in a vacuum Dewar 20. Of course, annular resistive magnets, C-magnets, and the like are also contemplated.

A whole body gradient coil assembly 30 includes x, y, and z-coils mounted along the bore 12 for generating gradient magnetic fields, Gx, Gy, and Gz. Preferably, the gradient coil assembly is a self-shielded gradient coil that includes primary x, y, and z-coil assemblies 32 potted in a dielectric former and secondary x, y, and z-coil assemblies 34 that are supported on a bore defining cylinder of the vacuum Dewar 20. A whole body radio frequency coil 36 can be mounted inside the gradient coil assembly 30. A whole body radio frequency shield 38, e.g., copper mesh, can be mounted between the whole body RF coil 36 and the gradient coil assembly 30. If desired, an insertable radio frequency coil 40 can be removably mounted in the bore in an examination region defined around an isocenter of the magnet to. In the embodiment of FIG. 2, the insertable radio frequency coil is a head and neck coil for imaging one or both of patient's head and neck, but other extremity coils can be provided, such as back coils for imaging the spine, knee coils, shoulder coils, breast coils, wrist coils and the like.

With continuing reference to FIG. 2, an operator interface and control station is provided that includes a human-readable display, such as a video monitor 52, and operator input devices such as a keyboard 54, a mouse 56, a trackball, light pen, or the like. A computer control and reconstruction module 58 is also provided that includes hardware and software for enabling the operator to select among a plurality of pre-programmed magnetic resonance sequences that are stored in a sequence control memory, if rf pulses are to be used as a part of the imaging study. A sequence controller 60 controls gradient amplifiers 62 connected with the gradient coil assembly 30 for causing the generation of the Gx, Gy, and Gz gradient magnetic fields at appropriate times during the selected gradient sequence and a digital transmitter 64 which causes a selected one of the whole body and insertable radio frequency coils to generate $B_1$ radio frequency field pulses at times appropriate to the selected sequence, if rf pulses are to be used in the study.

MR signals received by the coil 40 are demodulated by a digital receiver 66 and stored in a data memory 68. The data from the data memory are reconstructed by a reconstruction or array processor 70 into a volumetric image representation that is stored in an image memory 72. If a phased array is used as the receiving coil assembly, the image can be reconstructed from the coil signals. A video processor 74 under operator control converts selected portions of the volumetric image representation into slice images, projection images, perspective views, or the like as is conventional in the art for display on the video monitor.

Example—MKT™ Controller

Figure 3:
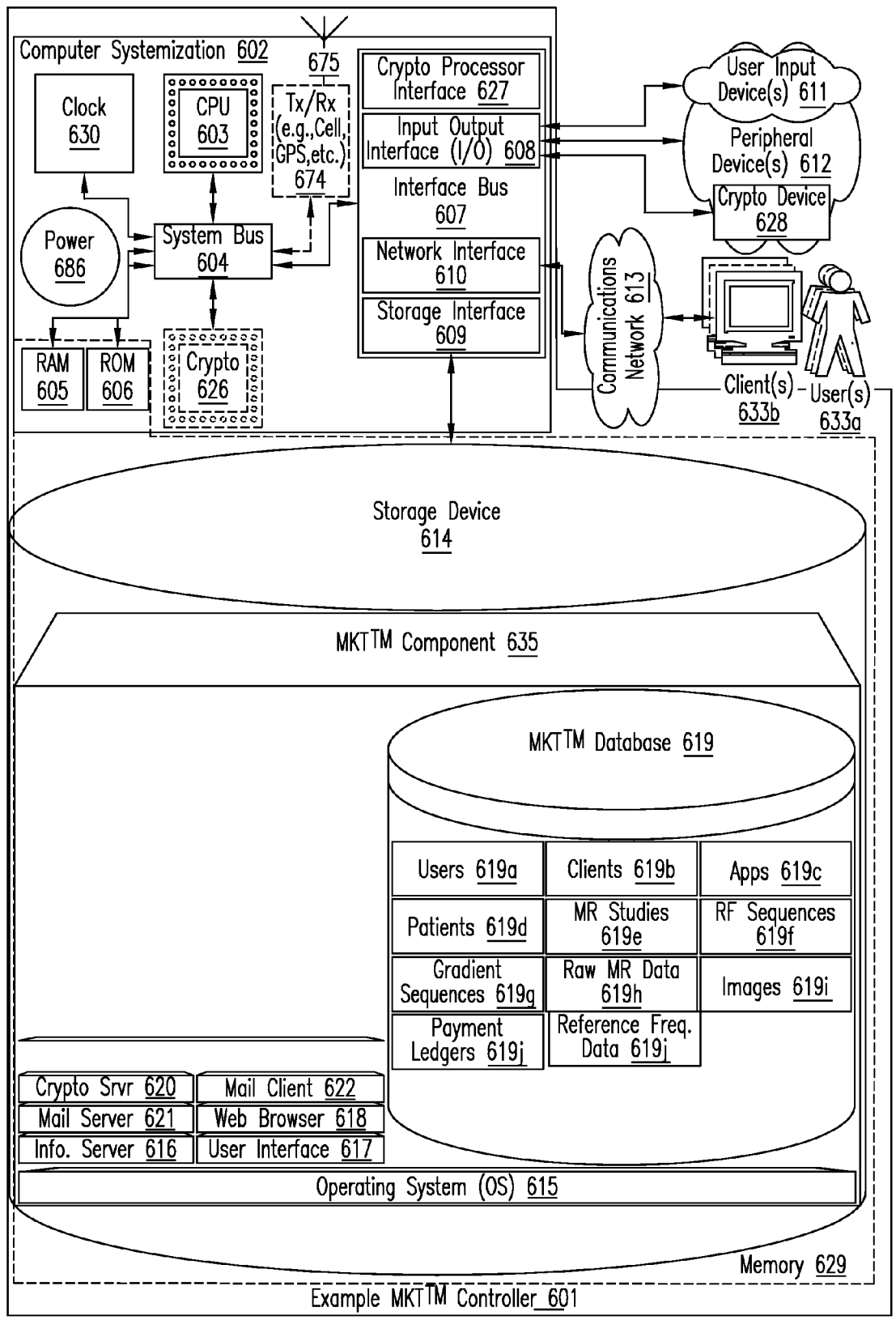
FIG. 3 depicts aspects of an exemplary computer system in accordance with the disclosure for operating a magnetic resonance system.

FIG. 3 illustrates inventive aspects of a MKT™ controller 601 for controlling a system such as that illustrated in FIG. 2 implementing some of the embodiments disclosed herein. In this embodiment, the MKT™ controller 601 may serve to aggregate, process, store, search, serve, identify, instruct, generate, match, and/or facilitate interactions with a computer through various technologies, and/or other related data.

Typically, a user or users, e.g., 633a, which may be people or groups of users and/or other systems, may engage information technology systems (e.g., computers) to facilitate operation of the system and information processing. In turn, computers employ processors to process information; such processors 603 may be referred to as central processing units (CPU). One form of processor is referred to as a microprocessor. CPUs use communicative circuits to pass binary encoded signals acting as instructions to enable various operations. These instructions may be operational and/or data instructions containing and/or referencing other instructions and data in various processor accessible and operable areas of memory 629 (e.g., registers, cache memory, random access memory, etc.). Such communicative instructions may be stored and/or transmitted in batches (e.g., batches of instructions) as programs and/or data components to facilitate desired operations. These stored instruction codes, e.g., programs, may engage the CPU circuit components and other motherboard and/or system components to perform desired operations. One type of program is a computer operating system, which, may be executed by CPU on a computer; the operating system enables and facilitates users to access and operate computer information technology and resources. Some resources that may be employed in information technology systems include: input and output mechanisms through which data may pass into and out of a computer; memory storage into which data may be saved; and processors by which information may be processed. These information technology systems may be used to collect data for later retrieval, analysis, and manipulation, which may be facilitated through a database program. These information technology systems provide interfaces that allow users to access and operate various system components.

In one embodiment, the MKT™ controller 601 may be connected to and/or communicate with entities such as, but not limited to: one or more users from user input devices 611; peripheral devices 612, components of the magnetic resonance system; an optional cryptographic processor device 628; and/or a communications network 613. For example, the MKT™ controller 601 may be connected to and/or communicate with users, e.g., 633a, operating client device(s), e.g., 633b, including, but not limited to, personal computer(s), server(s) and/or various mobile device(s) including, but not limited to, cellular telephone(s), smartphone(s) (e.g., iPhone®, Blackberry®, Android OS-based phones etc.), tablet computer(s) (e.g., Apple iPad™, HP Slate™, Motorola Xoom™, etc.), eBook reader(s) (e.g., Amazon Kindle™, Barnes and Noble's Nook™ eReader, etc.), laptop computer(s), notebook(s), netbook(s), gaming console(s)

(e.g., XBOX Live™, Nintendo® DS, Sony PlayStation® Portable, etc.), portable scanner(s) and/or the like.

Networks are commonly thought to comprise the interconnection and interoperation of clients, servers, and intermediary nodes in a graph topology. It should be noted that the term "server" as used throughout this application refers generally to a computer, other device, program, or combination thereof that processes and responds to the requests of remote users across a communications network. Servers serve their information to requesting "clients." The term "client" as used herein refers generally to a computer, program, other device, user and/or combination thereof that is capable of processing and making requests and obtaining and processing any responses from servers across a communications network. A computer, other device, program, or combination thereof that facilitates, processes information and requests, and/or furthers the passage of information from a source user to a destination user is commonly referred to as a "node." Networks are generally thought to facilitate the transfer of information from source points to destinations. A node specifically tasked with furthering the passage of information from a source to a destination is commonly called a "router." There are many forms of networks such as Local Area Networks (LANs), Pico networks, Wide Area Networks (WANs), Wireless Networks (WLANs), etc. For example, the Internet is generally accepted as being an interconnection of a multitude of networks whereby remote clients and servers may access and interoperate with one another.

The MKT™ controller 601 may be based on computer systems that may comprise, but are not limited to, components such as: a computer systemization 602 connected to memory 629.

Computer Systemization

A computer systemization 602 may comprise a clock 63o, central processing unit ("CPU(s)" and/or "processor(s)" (these terms are used interchangeable throughout the disclosure unless noted to the contrary)) 603, a memory 629 (e.g., a read only memory (ROM) 606, a random access memory (RAM) 605, etc.), and/or an interface bus 607, and most frequently, although not necessarily, are all interconnected and/or communicating through a system bus 604 on one or more (mother)board(s) 602 having conductive and/or otherwise transportive circuit pathways through which instructions (e.g., binary encoded signals) may travel to effect communications, operations, storage, etc. Optionally, the computer systemization may be connected to an internal power source 686; e.g., optionally the power source may be internal. Optionally, a cryptographic processor 626 and/or transceivers (e.g., ICs) 674 may be connected to the system bus. In another embodiment, the cryptographic processor and/or transceivers may be connected as either internal and/or external peripheral devices 612 via the interface bus I/O. In turn, the transceivers may be connected to antenna(s) 675, thereby effectuating wireless transmission and reception of various communication and/or sensor protocols; for example the antenna(s) may connect to: a Texas Instruments WiLink WL1283 transceiver chip (e.g., providing 802.11n, Bluetooth 3.0, FM, global positioning system (GPS) (thereby allowing MKT™ controller to determine its location)); Broadcom BCM4329FKUBG transceiver chip (e.g., providing 802.11n, Bluetooth 2.1+EDR, FM, etc.); a Broadcom BCM4750IUB8 receiver chip (e.g., GPS); an Infineon Technologies X-Gold 618-PMB9800 (e.g., providing 2G/3G HSDPA/HSUPA communications); and/or the like. The system clock typically has a crystal oscillator and generates a base signal through the computer systemization's circuit pathways. The clock is typically coupled to the system bus and various clock multipliers that will increase or decrease the base operating frequency for other components interconnected in the computer systemization. The clock and various components in a computer systemization drive signals embodying information throughout the system. Such transmission and reception of instructions embodying information throughout a computer systemization may be commonly referred to as communications. These communicative instructions may further be transmitted, received, and the cause of return and/or reply communications beyond the instant computer systemization to: communications networks, input devices, other computer systemizations, peripheral devices, and/or the like. Of course, any of the above components may be connected directly to one another, connected to the CPU, and/or organized in numerous variations employed as exemplified by various computer systems.

The CPU comprises at least one high-speed data processor adequate to execute program components for executing user and/or system-generated requests. Often, the processors themselves will incorporate various specialized processing units, such as, but not limited to: integrated system (bus) controllers, memory management control units, floating point units, and even specialized processing sub-units like graphics processing units, digital signal processing units, and/or the like. Additionally, processors may include internal fast access addressable memory, and be capable of mapping and addressing memory 629 beyond the processor itself; internal memory may include, but is not limited to: fast registers, various levels of cache memory (e.g., level 1, 2, 3, etc.), RAM, etc. The processor may access this memory through the use of a memory address space that is accessible via instruction address, which the processor can construct and decode allowing it to access a circuit path to a specific memory address space having a memory state. The CPU may be a microprocessor such as: AMD's Athlon, Duron and/or Opteron; ARM's application, embedded and secure processors; IBM and/or Motorola's DragonBall and PowerPC; IBM's and Sony's Cell processor; Intel's Celeron, Core (2) Duo, Itanium, Pentium, Xeon, and/or XScale; and/or the like processor(s). The CPU interacts with memory through instruction passing through conductive and/or transportive conduits (e.g., (printed) electronic and/or optic circuits) to execute stored instructions (i.e., program code) according to conventional data processing techniques. Such instruction passing facilitates communication within the MKT™ controller and beyond through various interfaces. Should processing requirements dictate a greater amount speed and/or capacity, distributed processors (e.g., Distributed MKT™ embodiments), mainframe, multi-core, parallel, and/or supercomputer architectures may similarly be employed. Alternatively, should deployment requirements dictate greater portability, smaller Personal Digital Assistants (PDAs) may be employed.

Depending on the particular implementation, features of the MKT™ implementations may be achieved by implementing a microcontroller such as CAST's R8051XC2 microcontroller; Intel's MCS 51 (i.e., 8051 microcontroller); and/or the like. Also, to implement certain features of the MKT™ embodiments, some feature implementations may rely on embedded components, such as: Application-Specific Integrated Circuit ("ASIC"), Digital Signal Processing ("DSP"), Field Programmable Gate Array ("FPGA"), and/or the like embedded technology. For example, any of the MKT™ component collection (distributed or otherwise) and/or features may be implemented via the microprocessor and/or via embedded components; e.g., via ASIC, coprocessor, DSP, FPGA, and/or the like. Alternately, some implementations of the MKT™ may be implemented with embedded components that are configured and used to achieve a variety of features or signal processing.

Depending on the particular implementation, the embedded components may include software solutions, hardware solutions, and/or some combination of both hardware/software solutions. For example, MKT™ features discussed herein may be achieved through implementing FPGAs, which are a semiconductor devices containing programmable logic components called "logic blocks", and programmable interconnects, such as the high performance FPGA Virtex series and/or the low cost Spartan series manufactured by Xilinx. Logic blocks and interconnects can be programmed by the customer or designer, after the FPGA is manufactured, to implement any of the MKT™ features. A hierarchy of programmable interconnects allow logic blocks to be interconnected as needed by the MKT™ system designer/administrator, somewhat like a one-chip programmable breadboard. An FPGA's logic blocks can be programmed to perform the function of basic logic gates such as AND, and XOR, or more complex combinational functions such as decoders or simple mathematical functions. In most FPGAs, the logic blocks also include memory elements, which may be simple flip-flops or more complete blocks of memory. In some circumstances, the MKT™ may be developed on regular FPGAs and then migrated into a fixed version that more resembles ASIC implementations. Alternate or coordinating implementations may migrate MKT™ controller features to a final ASIC instead of or in addition to FPGAs. Depending on the implementation all of the aforementioned embedded components and microprocessors may be considered the "CPU" and/or "processor" for the MKT™.

Power Source

The power source 686 may be of any standard form for powering small electronic circuit board devices such as the following power cells: alkaline, lithium hydride, lithium ion, lithium polymer, nickel cadmium, solar cells, and/or the like. Other types of AC or DC power sources may be used as well. In the case of solar cells, in one embodiment, the case provides an aperture through which the solar cell may capture photonic energy. The power cell 686 is connected to at least one of the interconnected subsequent components of the MKT™ thereby providing an electric current to all subsequent components. In one example, the power source 686 is connected to the system bus component 604. In an alternative embodiment, an outside power source 686 is provided through a connection across the I/O 608 interface. For example, a USB and/or IEEE 1394 connection carries both data and power across the connection and is therefore a suitable source of power.

Interface Adapters

Interface bus(ses) 607 may accept, connect, and/or communicate to a number of interface adapters, conventionally although not necessarily in the form of adapter cards, such as but not limited to: input output interfaces (I/O) 608, storage interfaces 609, network interfaces 610, and/or the like. Optionally, cryptographic processor interfaces 627 similarly may be connected to the interface bus. The interface bus provides for the communications of interface adapters with one another as well as with other components of the computer systemization. Interface adapters are adapted for a compatible interface bus. Interface adapters conventionally connect to the interface bus via a slot architecture. Conventional slot architectures may be employed, such as, but not limited to: Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and/or the like.

Storage interfaces 609 may accept, communicate, and/or connect to a number of storage devices such as, but not limited to: storage devices 614, removable disc devices, and/or the like. Storage interfaces may employ connection protocols such as, but not limited to: (Ultra) (Serial) Advanced Technology Attachment (Packet Interface) ((Ultra) (Serial) ATA(PI)), (Enhanced) Integrated Drive Electronics ((E)IDE), Institute of Electrical and Electronics Engineers (IEEE) 1394, fiber channel, Small Computer Systems Interface (SCSI), Universal Serial Bus (USB), and/or the like.

Network interfaces 610 may accept, communicate, and/or connect to a communications network 613. Through a communications network 613, the MKT™ controller is accessible through remote clients 633*b* (e.g., computers with web browsers) by users 633*a*. Network interfaces may employ connection protocols such as, but not limited to: direct connect, Ethernet (thick, thin, twisted pair 10/100/1000 Base T, and/or the like), Token Ring, wireless connection such as IEEE 802.11a-x, and/or the like. Should processing requirements dictate a greater amount speed and/or capacity, distributed network controllers (e.g., Distributed MKT™), architectures may similarly be employed to pool, load balance, and/or otherwise increase the communicative bandwidth required by the MKT™ controller. A communications network may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like. A network interface may be regarded as a specialized form of an input output interface. Further, multiple network interfaces 610 may be used to engage with various communications network types 613. For example, multiple network interfaces may be employed to allow for the communication over broadcast, multicast, and/or unicast networks.

Input Output interfaces (I/O) 608 may accept, communicate, and/or connect to user input devices 611, peripheral devices 612, cryptographic processor devices 628, and/or the like. I/O may employ connection protocols such as, but not limited to: audio: analog, digital, monaural, RCA, stereo, and/or the like; data: Apple Desktop Bus (ADB), IEEE 1394a-b, serial, universal serial bus (USB); infrared; joystick; keyboard; midi; optical; PC AT; PS/2; parallel; radio; video interface: Apple Desktop Connector (ADC), BNC, coaxial, component, composite, digital, Digital Visual Interface (DVI), high-definition multimedia interface (HDMI), RCA, RF antennae, S-Video, VGA, and/or the like; wireless transceivers: 802.11a/b/g/n/x; Bluetooth; cellular (e.g., code division multiple access (CDMA), high speed packet access (HSPA(+)), high-speed downlink packet access (HSDPA), global system for mobile communications (GSM), long term evolution (LTE), WiMax, etc.); and/or the like. One typical output device may include a video display, which typically comprises a Cathode Ray Tube (CRT) or Liquid Crystal Display (LCD) based monitor with an interface (e.g., DVI circuitry and cable) that accepts signals from a video interface, may be used. The video interface composites information generated by a computer systemization and generates video signals based on the composited information in a video memory frame. Another output device is a television set, which accepts signals from a video interface. Typically, the video interface provides the composited video information through a video connection interface that accepts a video display interface (e.g., an RCA composite video connector accepting an RCA composite video cable; a DVI connector accepting a DVI display cable, etc.).

User input devices 611 often are a type of peripheral device 612 (see below) and may include: card readers, dongles, finger print readers, gloves, graphics tablets, joysticks, keyboards, microphones, mouse (mice), remote controls, retina readers, touch screens (e.g., capacitive, resistive, etc.), trackballs, trackpads, sensors (e.g., accelerometers, ambient light, GPS, gyroscopes, proximity, etc.), styluses, and/or the like.

Peripheral devices 612, such as other components of the MR system, including signal generators in communication with RF coils, receivers in communication with RF coils, the gradient coil system, main magnet system and the like may be connected and/or communicate to I/O and/or other facilities of the like such as network interfaces, storage interfaces, directly to the interface bus, system bus, the CPU, and/or the like. Peripheral devices may be external, internal and/or part of the MKT™ controller. Peripheral devices may also include: antenna, audio devices (e.g., line-in, line-out, microphone input, speakers, etc.), cameras (e.g., still, video, webcam, etc.), dongles (e.g., for copy protection, ensuring secure transactions with a digital signature, and/or the like), external processors (for added capabilities; e.g., crypto devices 628), force-feedback devices (e.g., vibrating motors), network interfaces, printers, scanners, storage devices, transceivers (e.g., cellular, GPS, etc.), video devices (e.g., goggles for functional imaging, for example, monitors, etc.), video sources, visors, and/or the like. Peripheral devices often include types of input devices (e.g., cameras).

Cryptographic units such as, but not limited to, microcontrollers, processors 626, interfaces 627, and/or devices 628 may be attached, and/or communicate with the MKT™ controller. A MC68HC16 microcontroller, manufactured by Motorola Inc., may be used for and/or within cryptographic units. The MC68HC16 microcontroller utilizes a 16-bit multiply-and-accumulate instruction in the 16 MHz configuration and requires less than one second to perform a 512-bit RSA private key operation. Cryptographic units support the authentication of communications from interacting agents, as well as allowing for anonymous transactions. Cryptographic units may also be configured as part of CPU. Equivalent microcontrollers and/or processors may also be used. Other commercially available specialized cryptographic processors include: the Broadcom's CryptoNetX and other Security Processors; nCipher's nShield, SafeNet's Luna PCI (e.g., 7100) series; Semaphore Communications' 40 MHz Roadrunner 184; Sun's Cryptographic Accelerators (e.g., Accelerator 6000 PCIe Board, Accelerator 500 Daughtercard); Via Nano Processor (e.g., L2100, L2200, U2400) line, which is capable of performing 500+ MB/s of cryptographic instructions; VLSI Technology's 33 MHz 6868; and/or the like.

Memory

Generally, any mechanization and/or embodiment allowing a processor to affect the storage and/or retrieval of information is regarded as memory 629 (or 68, 72, etc.). However, memory is a fungible technology and resource, thus, any number of memory embodiments may be employed in lieu of or in concert with one another. It is to be understood that the MKT™ controller and/or a computer systemization may employ various forms of memory 629. For example, a computer systemization may be configured wherein the functionality of on-chip CPU memory (e.g., registers), RAM, ROM, and any other storage devices are provided by a paper punch tape or paper punch card mechanism; of course such an embodiment would result in an extremely slow rate of operation. In a typical configuration, memory 629 will include ROM 606, RAM 605, and a storage device 614. A storage device 614 may be any conventional computer system storage. Storage devices may include a drum; a (fixed and/or removable) magnetic disk drive; a magneto-optical drive; an optical drive (i.e., Blueray, CD ROM/RAM/Recordable (R)/ReWritable (RW), DVD R/RW, HD DVD R/RW etc.); an array of devices (e.g., Redundant Array of Independent Disks (RAID)); solid state memory devices (USB memory, solid state drives (SSD), etc.); other processor-readable storage mediums; and/or other devices of the like. Thus, a computer systemization generally requires and makes use of memory.

Component Collection

The memory 629 may contain a collection of program and/or database components and/or data such as, but not limited to: operating system component(s) 615 (operating system); information server component(s) 616 (information server); user interface component(s) 617 (user interface); Web browser component(s) 618 (Web browser); database(s) 619; mail server component(s) 621; mail client component(s) 622; cryptographic server component(s) 620 (cryptographic server) and/or the like (i.e., collectively a component collection). These components may be stored and accessed from the storage devices and/or from storage devices accessible through an interface bus. Although non-conventional program components such as those in the component collection, typically, are stored in a local storage device 614, they may also be loaded and/or stored in memory such as: peripheral devices, RAM, remote storage facilities through a communications network, ROM, various forms of memory, and/or the like.

Operating System

The operating system component 615 is an executable program component facilitating the operation of the MKT™ controller. Typically, the operating system facilitates access of I/O, network interfaces, peripheral devices, storage devices, and/or the like. The operating system may be a highly fault tolerant, scalable, and secure system such as: Apple Macintosh OS X (Server); AT&T Nan 9; Be OS; Unix and Unix-like system distributions (such as AT&T's UNIX; Berkley Software Distribution (BSD) variations such as FreeBSD, NetBSD, OpenBSD, and/or the like; Linux distributions such as Red Hat, Ubuntu, and/or the like); and/or the like operating systems. However, more limited and/or less secure operating systems also may be employed such as Apple Macintosh OS, IBM OS/2, Microsoft DOS, Microsoft Windows 2000/2003/3.1/95/98/CE/Millenium/NT/Vista/XP (Server), Palm OS, and/or the like. An operating system may communicate to and/or with other components in a component collection, including itself, and/or the like. Most frequently, the operating system communicates with other program components, user interfaces, and/or the like. For example, the operating system may contain, communicate, generate, obtain, and/or provide program component, system, user, and/or data communications, requests, and/or responses. The operating system, once executed by the CPU, may enable the interaction with communications networks, data, I/O, peripheral devices, program components, memory, user input devices, and/or the like. The operating system may provide communications protocols that allow the MKT™ controller to communicate with other entities through a communications network 613. Various communication protocols may be used by the MKT™ controller as a subcarrier transport mechanism for interaction, such as, but not limited to: multicast, TCP/IP, UDP, unicast, and/or the like.

Information Server

An information server component 616 is a stored program component that is executed by a CPU. The information server may be a conventional Internet information server such as, but not limited to Apache Software Foundation's Apache, Microsoft's Internet Information Server, and/or the like. The information server may allow for the execution of program components through facilities such as Active Server Page (ASP), ActiveX, (ANSI) (Objective-) C (++), C# and/or .NET, Common Gateway Interface (CGI) scripts, dynamic (D) hypertext markup language (HTML), FLASH, Java, JavaScript, Practical Extraction Report Language (PERL), Hypertext Pre-Processor (PHP), pipes, Python, wireless application protocol (WAP), WebObjects, and/or the like. The information server may support secure communications protocols such as, but not limited to, File Transfer Protocol (FTP); HyperText Transfer Protocol (HTTP); Secure Hypertext Transfer Protocol (HTTPS), Secure Socket Layer (SSL), messaging protocols (e.g., America Online (AOL) Instant Messenger (AIM), Application Exchange (APEX), ICQ, Internet Relay Chat (IRC), Microsoft Network (MSN) Messenger Service, Presence and Instant Messaging Protocol (PRIM), Internet Engineering Task Force's (IETF's) Session Initiation Protocol (SIP), SIP for Instant Messaging and Presence Leveraging Extensions (SIMPLE), open XML-based Extensible Messaging and Presence Protocol (XMPP) (i.e., Jabber or Open Mobile Alliance's (OMA's) Instant Messaging and Presence Service (IMPS)), Yahoo! Instant Messenger Service, and/or the like. The information server provides results in the form of Web pages to Web browsers, and allows for the manipulated generation of the Web pages through interaction with other program components. After a Domain Name System (DNS) resolution portion of an HTTP request is resolved to a particular information server, the information server resolves requests for information at specified locations on the MKT™ controller based on the remainder of the HTTP request. For example, a request such as http://123.124.125.126/myInformation.html might have the IP portion of the request "123.124.125.126" resolved by a DNS server to an information server at that IP address; that information server might in turn further parse the http request for the "/myInformation.html" portion of the request and resolve it to a location in memory containing the information "myInformation.html." Additionally, other information serving protocols may be employed across various ports, e.g., FTP communications across port 21, and/or the like. An information server may communicate to and/or with other components in a component collection, including itself, and/or facilities of the like. Most frequently, the information server communicates with the MKT™ database 619, operating systems, other program components, user interfaces, Web browsers, and/or the like.

Access to the MKT™ database may be achieved through a number of database bridge mechanisms such as through scripting languages as enumerated below (e.g., CGI) and through inter-application communication channels as enumerated below (e.g., CORBA, WebObjects, etc.). Any data requests through a Web browser are parsed through the bridge mechanism into appropriate grammars as required by the MKT™. In one embodiment, the information server would provide a Web form accessible by a Web browser. Entries made into supplied fields in the Web form are tagged as having been entered into the particular fields, and parsed as such. The entered terms are then passed along with the field tags, which act to instruct the parser to generate queries directed to appropriate tables and/or fields. In one embodiment, the parser may generate queries in standard SQL by instantiating a search string with the proper join/select commands based on the tagged text entries, wherein the resulting command is provided over the bridge mechanism to the MKT™ as a query. Upon generating query results from the query, the results are passed over the bridge mechanism, and may be parsed for formatting and generation of a new results Web page by the bridge mechanism. Such a new results Web page is then provided to the information server, which may supply it to the requesting Web browser.

Also, an information server may contain, communicate, generate, obtain, and/or provide program component, system, user, and/or data communications, requests, and/or responses.

User Interface

Computer interfaces in some respects are similar to automobile operation interfaces. Automobile operation interface elements such as steering wheels, gearshifts, and speedometers facilitate the access, operation, and display of automobile resources, and status. Computer interaction interface elements such as check boxes, cursors, menus, scrollers, and windows (collectively and commonly referred to as widgets) similarly facilitate the access, capabilities, operation, and display of data and computer hardware and operating system resources, and status. Operation interfaces are commonly called user interfaces. Graphical user interfaces (GUIs) such as the Apple Macintosh Operating System's Aqua, IBM's OS/2, Microsoft's Windows 2000/2003/3.1/95/98/CE/Millenium/NT/XP/Vista/7 (i.e., Aero), Unix's X-Windows (e.g., which may include additional Unix graphic interface libraries and layers such as K Desktop Environment (KDE), mythTV and GNU Network Object Model Environment (GNOME)), web interface libraries (e.g., ActiveX, AJAX, (D)HTML, FLASH, Java, JavaScript, etc. interface libraries such as, but not limited to, Dojo, jQuery(UI), MooTools, Prototype, script.aculo.us, SWFObject, Yahoo! User Interface, any of which may be used and) provide a baseline and means of accessing and displaying information graphically to users.

A user interface component 617 is a stored program component that is executed by a CPU. The user interface may be a conventional graphic user interface as provided by, with, and/or atop operating systems and/or operating environments such as already discussed. The user interface may allow for the display, execution, interaction, manipulation, and/or operation of program components and/or system facilities through textual and/or graphical facilities. The user interface provides a facility through which users may affect, interact, and/or operate a computer system. A user interface may communicate to and/or with other components in a component collection, including itself, and/or facilities of the like. Most frequently, the user interface communicates with operating systems, other program components, and/or the like. The user interface may contain, communicate, generate, obtain, and/or provide program component, system, user, and/or data communications, requests, and/or responses.

Web Browser

A Web browser component 618 is a stored program component that is executed by a CPU. The Web browser may be a conventional hypertext viewing application such as Microsoft Internet Explorer or Netscape Navigator. Secure Web browsing may be supplied with 128 bit (or greater) encryption by way of HTTPS, SSL, and/or the like. Web browsers allowing for the execution of program components through facilities such as ActiveX, AJAX, (D)HTML, FLASH, Java, JavaScript, web browser plug-in APIs (e.g., FireFox, Safari Plug-in, and/or the like APIs), and/or the like. Web browsers and like information access tools may be integrated into PDAs, cellular telephones, and/or other mobile devices. A Web browser may communicate to and/or with other components in a component collection, including itself, and/or facilities of the like. Most frequently, the Web browser communicates with information servers, operating systems, integrated program components (e.g., plug-ins), and/or the like; e.g., it may contain, communicate, generate, obtain, and/or provide program component, system, user, and/or data communications, requests, and/or responses. Of course, in place of a Web browser and information server, a combined application may be developed to perform similar functions of both. The combined application would similarly affect the obtaining and the provision of information to users, user agents, and/or the like from the MKT™ enabled nodes. The combined application may be nugatory on systems employing standard Web browsers.

Mail Server

A mail server component 621 is a stored program component that is executed by a CPU 603. The mail server may be a conventional Internet mail server such as, but not limited to sendmail, Microsoft Exchange, and/or the like. The mail server may allow for the execution of program components through facilities such as ASP, ActiveX, (ANSI) (Objective-) C (++), C# and/or .NET, CGI scripts, Java, JavaScript, PERL, PHP, pipes, Python, WebObjects, and/or the like. The mail server may support communications protocols such as, but not limited to: Internet message access protocol (IMAP), Messaging Application Programming Interface (MAPI)/Microsoft Exchange, post office protocol (POP3), simple mail transfer protocol (SMTP), and/or the like. The mail server can route, forward, and process incoming and outgoing mail messages that have been sent, relayed and/or otherwise traversing through and/or to the MKT™.

Access to the MKT™ mail may be achieved through a number of APIs offered by the individual Web server components and/or the operating system.

Also, a mail server may contain, communicate, generate, obtain, and/or provide program component, system, user, and/or data communications, requests, information, and/or responses.

Mail Client

A mail client component 622 is a stored program component that is executed by a CPU 603. The mail client may be a conventional mail viewing application such as Apple Mail, Microsoft Entourage, Microsoft Outlook, Microsoft Outlook Express, Mozilla, Thunderbird, and/or the like. Mail clients may support a number of transfer protocols, such as: IMAP, Microsoft Exchange, POP3, SMTP, and/or the like. A mail client may communicate to and/or with other components in a component collection, including itself, and/or facilities of the like. Most frequently, the mail client communicates with mail servers, operating systems, other mail clients, and/or the like; e.g., it may contain, communicate, generate, obtain, and/or provide program component, system, user, and/or data communications, requests, information, and/or responses. Generally, the mail client provides a facility to compose and transmit electronic mail messages.

Cryptographic Server

A cryptographic server component 62o is a stored program component that is executed by a CPU 603, cryptographic processor 626, cryptographic processor interface 627, cryptographic processor device 628, and/or the like. Cryptographic processor interfaces will allow for expedition of encryption and/or decryption requests by the cryptographic component; however, the cryptographic component, alternatively, may run on a conventional CPU. The cryptographic component allows for the encryption and/or decryption of provided data. The cryptographic component allows for both symmetric and asymmetric (e.g., Pretty Good Protection (PGP)) encryption and/or decryption. The cryptographic component may employ cryptographic techniques such as, but not limited to: digital certificates (e.g., X.509 authentication framework), digital signatures, dual signatures, enveloping, password access protection, public key management, and/or the like. The cryptographic component will facilitate numerous (encryption and/or decryption) security protocols such as, but not limited to: checksum, Data Encryption Standard (DES), Elliptical Curve Encryption (ECC), International Data Encryption Algorithm (IDEA), Message Digest 5 (MD5, which is a one way hash function), passwords, Rivest Cipher (RC5), Rijndael, RSA (which is an Internet encryption and authentication system that uses an algorithm developed in 1977 by Ron Rivest, Adi Shamir, and Leonard Adleman), Secure Hash Algorithm (SHA), Secure Socket Layer (SSL), Secure Hypertext Transfer Protocol (HTTPS), and/or the like. Employing such encryption security protocols, the MKT™ may encrypt all incoming and/or outgoing communications and may serve as node within a virtual private network (VPN) with a wider communications network. The cryptographic component facilitates the process of "security authorization" whereby access to a resource is inhibited by a security protocol wherein the cryptographic component effects authorized access to the secured resource. In addition, the cryptographic component may provide unique identifiers of content, e.g., employing and MD5 hash to obtain a unique signature for an digital audio file. A cryptographic component may communicate to and/or with other components in a component collection, including itself, and/or facilities of the like. The cryptographic component supports encryption schemes allowing for the secure transmission of information across a communications network to enable the MKT™ component to engage in secure transactions if so desired. The cryptographic component facilitates the secure accessing of resources on the MKT™ and facilitates the access of secured resources on remote systems; i.e., it may act as a client and/or server of secured resources. Most frequently, the cryptographic component communicates with information servers, operating systems, other program components, and/or the like. The cryptographic component may contain, communicate, generate, obtain, and/or provide program component, system, user, and/or data communications, requests, and/or responses.

The MKT™ Database

The MKT™ database component 619 may be embodied in a database and its stored data. The database is a stored program component, which is executed by the CPU; the stored program component portion configuring the CPU to process the stored data. The database may be a conventional, fault tolerant, relational, scalable, secure database such as Oracle or Sybase. Relational databases are an extension of a flat file. Relational databases consist of a series of related tables. The tables are interconnected via a key field. Use of the key field allows the combination of the tables by indexing against the key field; i.e., the key fields act as dimensional pivot points for combining information from various tables. Relationships generally identify links maintained between tables by matching primary keys. Primary keys represent fields that uniquely identify the rows of a table in a relational database. More precisely, they uniquely identify rows of a table on the "one" side of a one-to-many relationship.

Alternatively, the MKT™ database may be implemented using various standard data-structures, such as an array, hash, (linked) list, struct, structured text file (e.g., XML), table, and/or the like. Such data-structures may be stored in memory and/or in (structured) files. In another alternative, an object-oriented database may be used, such as Frontier, ObjectStore, Poet, Zope, and/or the like. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the MKT™ database is implemented as a data-structure, the use of the MKT™ database 619 may be integrated into another component such as the MKT™ component 635. Also, the database may be implemented as a mix of data structures, objects, and relational structures. Databases may be consolidated and/or distributed in countless variations through standard data processing techniques. Portions of databases, e.g., tables, may be exported and/or imported and thus decentralized and/or integrated.

In one embodiment, the database component 619 includes several tables 619a-j. A Users (e.g., operators and physicians) table 619a may include fields such as, but not limited to: user_id, ssn, dob, first_name, last_name, age, state, address_firstline, address_secondline, zipcode, devices_list, contact_info, contact_type, alt contact_info, alt contact_type, and/or the like to refer to any type of enterable data or selections discussed herein. The Users table may support and/or track multiple entity accounts. A Clients table 619b may include fields such as, but not limited to: user_id, client_id, client_ip, client_type, client_model, operating_system, os_version, app_installed_flag, and/or the like. An Apps table 619c may include fields such as, but not limited to: app_ID, app_name, app_type, OS_compatibilities_list, version, timestamp, developer_ID, and/or the like. A Patients table for patients associated with an entity administering the magnetic resonance system 619d may include fields such as, but not limited to: patient_id, patient_name, patient address, ip_address, mac_address, auth_key, port_num, security settings_list, and/or the like. An MR Studies table 619e may include fields such as, but not limited to: study_, study_name, security_settings_list, study_parameters, rf_sequences, gradient_sequences, coil_selection, imaging_mode, and/or the like. An RF sequences table 619f including a plurality of different rf pulse sequences may include fields such as, but not limited to: sequence_type, sequence_id, tip_angle, coil_selection, power_level, and/or the like. A gradient sequences table 619g may include fields relating to different gradient field sequences such as, but not limited to: sequence_id, Gx, Gy, Gz, Gxy, Gxz, Gyz, Gxyz, field strength, time_duration, and/or the like. A raw MR data table 619h may include fields such as, but not limited to: study_id, time_stamp, file_size, patient_id, rf_sequence, body_part_imaged, slice_id, and/or the like. A Images table 619i may include fields such as, but not limited to: image_id, study_id, file_size, patient_id, time_stamp, settings, and/or the like. A Payment Legers table 619j may include fields such as, but not limited to: request_id, timestamp, payment_amount, batch_id, transaction_id, clear_flag, deposit_account, transaction_summary, patient_name, patient_account, and/or the like.

In one embodiment, user programs may contain various user interface primitives, which may serve to update the MKT™ platform. Also, various accounts may require custom database tables depending upon the environments and the types of clients the MKT™ system may need to serve. It should be noted that any unique fields may be designated as a key field throughout. In an alternative embodiment, these tables have been decentralized into their own databases and their respective database controllers (i.e., individual database controllers for each of the above tables). Employing standard data processing techniques, one may further distribute the databases over several computer systemizations and/or storage devices. Similarly, configurations of the decentralized database controllers may be varied by consolidating and/or distributing the various database components 619a-j. The MKT™ system may be configured to keep track of various settings, inputs, and parameters via database controllers.

The MKT™ database may communicate to and/or with other components in a component collection, including itself, and/or facilities of the like. Most frequently, the MKT™ database communicates with the MKT™ component, other program components, and/or the like. The database may contain, retain, and provide information regarding other nodes and data.

The MKT™ Components

The MKT™ component 635 is a stored program component that is executed by a CPU. In one embodiment, the MKT™ component incorporates any and/or all combinations of the aspects of the MKT™ systems discussed in the figures of this disclosure. As such, the MKT™ component affects accessing, obtaining and the provision of information, services, transactions, and/or the like across various communications networks.

The MKT™ component may transform raw data collected by the magnetic resonance system into at least one of (i) an image, (ii) dynamic flow data, (iii) perfusion data, (iii) spectroscopic identity of chemical species, (iv) physiological data, or (v) metabolic data, among other things. In one embodiment, the MKT™ component 635 takes inputs (e.g., digitized representations of Mxy signals produced by RD or SR pulses, and transforms the inputs via various components of the system, into outputs (e.g., (i) an image, (ii) dynamic flow data, (iii) perfusion data, (iii) spectroscopic identity of chemical species, (iv) physiological data, or (v) metabolic data, among other things).

The MKT™ component enabling access of information between nodes may be developed by employing standard development tools and languages such as, but not limited to: Apache components, Assembly, ActiveX, binary executables, (ANSI) (Objective-) C (++), C# and/or .NET, database adapters, CGI scripts, Java, JavaScript, mapping tools, procedural and object oriented development tools, PERL, PHP, Python, shell scripts, SQL commands, web application server extensions, web development environments and libraries (e.g., Microsoft's ActiveX; Adobe AIR, FLEX & FLASH; AJAX; (D)HTML; Dojo, Java; JavaScript; jQuery(UI); MooTools; Prototype; script.aculo.us; Simple Object Access Protocol (SOAP); SWFObject; Yahoo! User Interface; and/or the like), WebObjects, and/or the like. In one embodiment, the MKT™ server employs a cryptographic server to encrypt and decrypt communications. The MKT™ component may communicate to and/or with other components in a component collection, including itself, and/or facilities of the like. Most frequently, the MKT™ component communicates with the MKT™ database, operating systems, other program components, and/or the like. The MKT™ may contain, communicate, generate, obtain, and/or provide program component, system, user, and/or data communications, requests, and/or responses.

Distributed MKT™ Embodiments

The structure and/or operation of any of the MKT™ node controller components may be combined, consolidated, and/or distributed in any number of ways to facilitate development and/or deployment. Similarly, the component collection may be combined in any number of ways to facilitate deployment and/or development. To accomplish this, one may integrate the components into a common code base or in a facility that can dynamically load the components on demand in an integrated fashion.

The component collection may be consolidated and/or distributed in countless variations through standard data processing and/or development techniques. Multiple instances of any one of the program components in the program component collection may be instantiated on a single node, and/or across numerous nodes to improve performance through load-balancing and/or data-processing techniques. Furthermore, single instances may also be distributed across multiple controllers and/or storage devices; e.g., databases. All program component instances and controllers working in concert may do so through standard data processing communication techniques.

The configuration of the MKT™ controller will depend on the context of system deployment. Factors such as, but not limited to, the budget, capacity, location, and/or use of the underlying hardware resources may affect deployment requirements and configuration. Regardless of if the configuration results in more consolidated and/or integrated program components, results in a more distributed series of program components, and/or results in some combination between a consolidated and distributed configuration, data may be communicated, obtained, and/or provided. Instances of components consolidated into a common code base from the program component collection may communicate, obtain, and/or provide data. This may be accomplished through intra-application data processing communication techniques such as, but not limited to: data referencing (e.g., pointers), internal messaging, object instance variable communication, shared memory space, variable passing, and/or the like.

If component collection components are discrete, separate, and/or external to one another, then communicating, obtaining, and/or providing data with and/or to other component components may be accomplished through inter-application data processing communication techniques such as, but not limited to: Application Program Interfaces (API) information passage; (distributed) Component Object Model ((D)COM), (Distributed) Object Linking and Embedding ((D)OLE), and/or the like), Common Object Request Broker Architecture (CORBA), Jini local and remote application program interfaces, JavaScript Object Notation (JSON), Remote Method Invocation (RMI), SOAP, process pipes, shared files, and/or the like. Messages sent between discrete component components for inter-application communication or within memory spaces of a singular component for intra-application communication may be facilitated through the creation and parsing of a grammar. A grammar may be developed by using development tools such as lex, yacc, XML, and/or the like, which allow for grammar generation and parsing capabilities, which in turn may form the basis of communication messages within and between components.

For example, a grammar may be arranged to recognize the tokens of an HTTP post command, e.g.:

w3c-post http:// . . . Value1 where Value1 is discerned as being a parameter because "http://" is part of the grammar syntax, and what follows is considered part of the post value. Similarly, with such a grammar, a variable "Value1" may be inserted into an "http://" post command and then sent. The grammar syntax itself may be presented as structured data that is interpreted and/or otherwise used to generate the parsing mechanism (e.g., a syntax description text file as processed by lex, yacc, etc.). Also, once the parsing mechanism is generated and/or instantiated, it itself may process and/or parse structured data such as, but not limited to: character (e.g., tab) delineated text, HTML, structured text streams, XML, and/or the like structured data. In another embodiment, inter-application data processing protocols themselves may have integrated and/or readily available parsers (e.g., JSON, SOAP, and/or like parsers) that may be employed to parse (e.g., communications) data. Further, the parsing grammar may be used beyond message parsing, but may also be used to parse: databases, data collections, data stores, structured data, and/or the like. Again, the desired configuration will depend upon the context, environment, and requirements of system deployment.

For example, in some implementations, the MKT™ controller may be executing a PHP script implementing a Secure Sockets Layer ("SSL") socket server via the information server, which listens to incoming communications on a server port to which a client may send data, e.g., data encoded in JSON format. Upon identifying an incoming communication, the PHP script may read the incoming message from the client device, parse the received JSON-encoded text data to extract information from the JSON-encoded text data into PHP script variables, and store the data (e.g., client identifying information, etc.) and/or extracted information in a relational database accessible using the Structured Query Language ("SQL"). An exemplary listing, written substantially in the form of PHP/SQL commands, to accept JSON-encoded input data from a client device via a SSL connection, parse the data to extract variables, and store the data to a database, is provided below:

```
<?PHP
header('Content-Type: text/plain');
// set ip address and port to listen to for incoming data
$address = '192.168.0.100';
$port = 255;
// create a server-side SSL socket, listen for/accept incoming
communication
$sock = socket_create(AF_INET, SOCK_STREAM, 0);
socket_bind($sock, $address, $port) or die('Could not bind to address');
socket_listen($sock);
$client = socket_accept($sock);
// read input data from client device in 1024 byte blocks until end of
message do {
        $input = "";
        $input = socket_read($client, 1024);
        $data .= $input;
} while($input != "");
// parse data to extract variables
$obj = json_decode($data, true);
// store input data in a database
mysql_connect("201.408.185.132",$DBserver,$password); // access
database server
mysql_select("CLIENT_DB.SQL"); // select database to append
mysql_query("INSERT INTO UserTable (transmission)
VALUES ($data)"); // add data to UserTable table in a CLIENT database
mysql_close("CLIENT_DB.SQL"); // close connection to database
?>
```

Also, the following resources may be used to provide example embodiments regarding SOAP parser implementation:

http://www.xay.com/perl/site/lib/SOAP/Parser.html
http://publib.boulder.ibm.com/infocenter/tivihelp/v2r1/index.jsp?topic=/com.ibm.IBMDI.doc/referenceguide295.htm and other parser implementations:

http://publib.boulder.ibm.com/infocenter/tivihelp/v2r1/index.jsp?topic=/com.ibm.IBMDI.doc/referenceguide259.htm all of which are hereby expressly incorporated by reference.

In order to address various issues and advance the art, the entirety of this application for MKT™ APPARATUSES, METHODS AND SYSTEMS (including the Cover Page, Title, Headings, Field, Background, Summary, Brief Description of the Drawings, Detailed Description, Claims, Abstract, Figures, Appendices and/or otherwise) shows by way of illustration various embodiments in which the claimed inventions may be practiced. The advantages and features of the application are of a representative sample of embodiments only, and are not exhaustive and/or exclusive. They are presented only to assist in understanding and teach the claimed principles. It should be understood that they are not representative of all disclosed embodiments. As such, certain aspects of the disclosure have not been discussed herein. That alternate embodiments may not have been presented for a specific portion of the invention or that further undescribed alternate embodiments may be available for a portion is not to be considered a disclaimer of those alternate embodiments. It will be appreciated that many of those undescribed embodiments incorporate the same principles of the invention and others are equivalent. Thus, it is to be understood that other embodiments may be utilized and functional, logical, organizational, structural and/or topological modifications may be made without departing from the scope and/or spirit of the disclosure. As such, all examples and/or embodiments are deemed to be non-limiting throughout this disclosure. Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure. Furthermore, it is to be understood that such features are not limited to serial execution, but rather, any number of threads, processes, services, servers, and/or the like that may execute asynchronously, concurrently, in parallel, simultaneously, synchronously, and/or the like are contemplated by the disclosure. As such, some of these features may be mutually contradictory, in that they cannot be simultaneously present in a single embodiment. Similarly, some features are applicable to one aspect of the invention, and inapplicable to others. In addition, the disclosure includes other inventions not presently claimed. Applicant reserves all rights in those presently unclaimed inventions including the right to claim such inventions, file additional applications, continuations, continuations in part, divisions, and/or the like thereof. As such, it should be understood that advantages, embodiments, examples, functional, features, logical, organizational, structural, topological, and/or other aspects of the disclosure are not to be considered limitations on the disclosure as defined by the claims or limitations on equivalents to the claims. It is to be understood that, depending on the particular needs and/or characteristics of a MKT™ individual and/or enterprise user, database configuration and/or relational model, data type, data transmission and/or network framework, syntax structure, and/or the like, various embodiments of the MKT™ may be implemented that enable a great deal of flexibility and customization.

Further Implementations

In various further aspects, the disclosure provides further implementations of methods, systems and machine readable programs that are related with the above disclosure.

1. Sensitive Detection of Molecules

One innovation disclosed herein is the use of certain SR conditions to sensitively detect the presence (or lack thereof) of a given molecule. NMR spectroscopy is well known in the art as a method of detecting the presence of a given molecule. The usual method for doing this is to put the sample or subject to be investigated a high field magnet with an associated NMR probe. Using well known NMR techniques, the nuclear magnetism of the molecules in the sample or subject may be manipulated to produce frequency dependent spectra. These spectra can be compared to existing databases to determine the presence and concentration of a given molecule.

This works well when a) the molecules of interest are soluble in a solvent suitable for use in an NMR study (solid state spectroscopy is also possible but more limited in scope), b) there are sufficient molecules in solution to carry out the necessary NMR protocols, c) the molecules' NMR spectrum is not too complicated and d) there is sufficient time to carry out the necessary NMR studies. However in practice one of these factors often limits the applicability of NMR to identify the presence of a molecule.

In accordance with a further aspect of the disclosure, embodiments are provided that overcome these drawbacks by exploiting properties of the superradiant condition. Specifically, the disclosed embodiments permit the presence of a given molecule to be determined a) at levels of concentration lower than those achievable and b) more rapidly than using present day NMR. In addition, the methods, systems and programs apply equally well to solids as to liquids, thus removing the limitation for high resolution NMR that the samples be in solution.

In ordinary NMR, the frequency position of peaks in the spectra from various nuclei (typically $^1$H, $^{13}$C, $^{15}$N etc) do not depend on the number of nuclei present. That is, the peaks may get larger with an increase in concentration of the molecule under investigation, but they do not change their position in the frequency spectrum. By contrast, the SR effect is a cooperative phenomenon. The peaktime width of the SR pulse changes depending on the number of identical nuclei in a given sample or subject.

Equation 20 in the previous section implies that that the width and peaktime of an SR pulse is a function of the resonant frequency of the nuclei in a molecule as well as its concentration. Furthermore, in the limit where $\tau_R \rightarrow T_2$ $t_o$ is a strong function of $\tau_R$ which is in turn, assuming all other variables are held constant, a function of $M_o \sim N$ where N is the number of molecules in the FOV of the FEC. Thus, under certain circumstances changing the number of molecules of a given species in a study FOV can produce very sensitive changes in the resultant SR pulse. As a non exclusive example, a system of molecules that is held at or near the transition point between the normal and SR regimes is very sensitive to the addition of molecules of the same species.

Figure 4A:
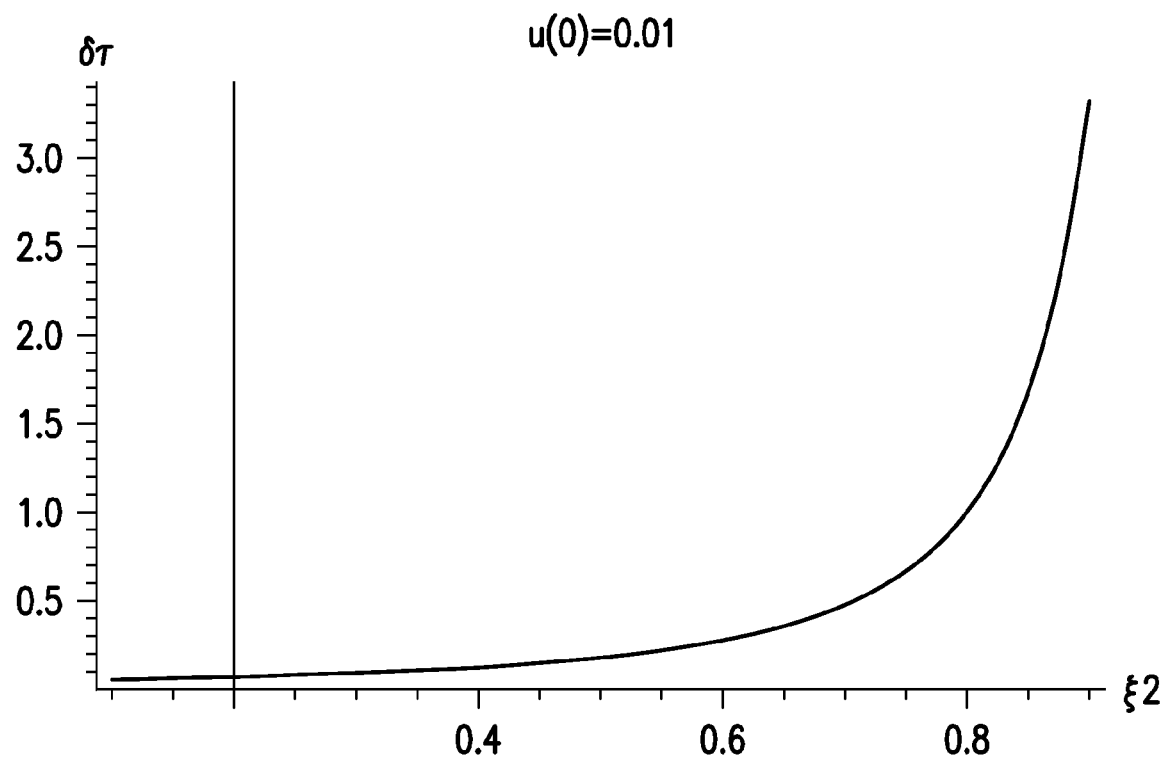
FIG. 4A illustrates the change in width of the pulse τ as the SR transition is approach ($\xi 2 \rightarrow 1$) for an initial x-y magnetization of 0.01.
Figure 4B:
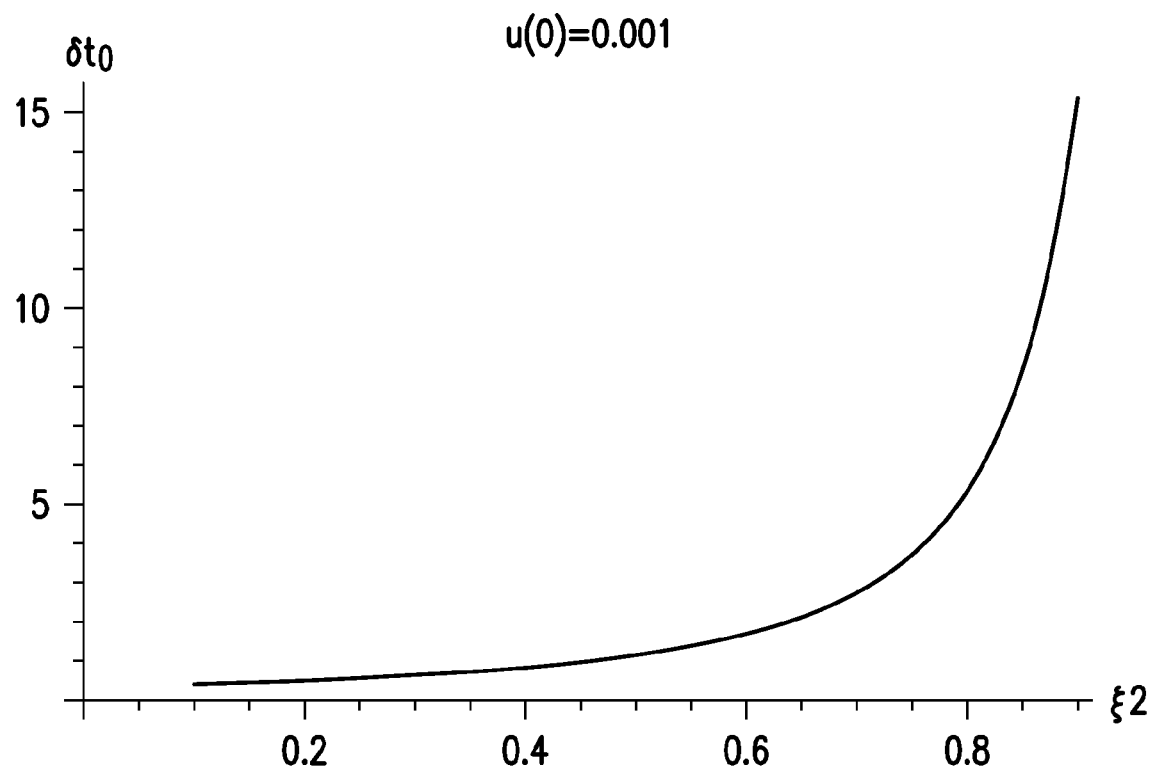
FIG. 4B illustrates change in peaktime of the pulse as the SR transition is approach ($\xi 2 \rightarrow 1$) for an initial x-y magnetization of 0.001.

Applicant has discovered that the transition from the normal MR regime (where nuclear magnetization decays exponentially with time constant $T_1$) and SR MR can be easily distinguished. For example, near the SR transition, the peaktime and width of the SR pulse are very sensitive to changes in nuclear magnetism (FIGS. 4A-4B). Nuclear magnetism is itself directly proportional to the number of spins present in the sample or subject so this, in turn, becomes a sensitive measure of the number of spins in a sample or subject.

Applicant has further discovered that, by changing the features of the FEC, the magnetic field gradient, the flip angle of the initial RF pulse, the type and number of molecules in the SSR, or a combination of all of these, a given concentration of nuclei can be kept at or very near the transition point between the two regimes. These parameters can be controlled very precisely to closely define the normal to SR transition point for a given sample or subject. That is, for a given nuclei at a given concentration, there is a value of the probe quality factor Q, gradient G, and RF pulse excitation angle for which the sample or subject is at, or very near, the transition point between the normal and superradiant regimes.

As an example, in vivo serotonin concentrations in brain have been shown to be low in patients with depression and increase with administration of various anti-depressants in a cohort of patients. Determining serotonin levels in blood do not represent values in brain. Although the serotonin metabolite 5 HIAA can be measured in the cerebrospinal fluid (CSF), this is much more difficult to access. While changes in serotonin concentration as a result of various drug therapies can be quite sharp, the overall concentration of in vivo serotonin (~ng/ml) remains too low to be detectable in conventional MRS studies. Thus, a technique that could improve MR sensitivity to detect these low concentrations of serotonin may be helpful in identifying subjects Who may benefit from antidepressant therapy. Also, the small changes in the concentration of serotonin in vivo could be used to monitor the therapeutic response of subjects. In one implementation, the SSR is filled with a known amount of serotonin or a similar target molecule and the FM or other system parameters such as local field gradients adjusted so that so that the condition $\tau_R \sim T_2$ is achieved for the molecule in the SSR. Via application of one or more RF pulses, an SR pulse is produced from the target molecules in the SSR; the features of this pulse such as its width, peak time etc are stored. Then a subject may be inserted in the MR device and an identical RF pulse sequence used to produce a pulse from both the target molecules in the SSR and the subject. The resulting change in the features of the subsequent SR pulse may be used to determine the overall change in number of target molecules that resulted from insertion of the subject into the MR device, this can then be used to determine concentration levels of that target molecule in the subject.

This process can be carried out singly or multiple times as desired. It may also be combined with various other pulse sequences to suppress unwanted resonances in the subject or sample. In one embodiment standard RF pulse sequences such as WATERGATE, that are known in the art, or other methods disclosed herein can be used to substantially eliminate signal from water prior to carrying out the above sequence.

The process can also be implemented in conjunction with various calibration schemes. For example, the nuclei in the SSR can be characterized prior to introduction of the sample or subject by carrying out multiple SR pulse sequences with different gains and phase angles settings for the FEC. Thus, the response of the nuclei in the SSR can be characterized under a wide variety of circumstances allowing for greater accuracy in identification and quantification of target molecules during the actual study. Another embodiment would comprise introducing into the MR device, along with the SSR, a number of dummy samples containing various concentrations of the target molecule in phantoms that simulate the actual subject or sample environment. In this way the response of the system to a subject or sample containing an unknown amount of the target molecule can be calibrated against the data obtained this calibration step.

Thus, in one embodiment a method and related system and machine readable program are provided for detecting the presence of a set of nuclei, molecules, molecular fragments, proteins and the like. This can include preparing a control sample consisting in part or in whole of a molecule or molecules with known composition and concentration, as well as system components and machine readable programs that facilitate the same. The disclosed embodiments can further include controlling at least one external parameter such as the ambient magnetic field, magnetic field gradient, quality factor of the NMR coil, and RF pulse angle so as to maintain the control sample at or near its SR transition. The method can further include bringing into proximity with the control sample a target sample containing a molecule or molecules of unknown composition and concentration, and causing both the control sample and target sample to be subjected to RF excitation so as to cause the magnetic moment of at least one set of nuclei to have an angle greater than 90° with respect to the ambient magnetic field. The embodiments can still further include adjusting at least one ambient condition such as the magnetic field gradient so as to establish the change in the SR transition, and determining the composition and concentration of said target molecule or molecules by analyzing the data. The disclosed embodiments can be combined with and/or employ equipment discussed herein above.

As demonstrated herein, the SR state is not one that occurs under normal clinical MRSI conditions. We therefore teach the inclusion in the MR machine of a coil whose electronic circuitry has been configured so as to amplify any feedback field henceforth referred to as the Feedback Enabled Coil (FEC) and of a volume, henceforth to be referred to as the Supplementary Spin Reservoir (SSR). The role of the SSR is to facilitate the production of SR conditions so that the properties of the SR state (described below) may be more fully exploited for the purposes of improving one or more MR studies, imaging protocols, spectroscopic analyses, etc. In a preferred embodiment, the SSR is a container with a predetermined concentration of one or more molecules that will be the target molecule(s) of the SR MRS. The SSR is situated ex vivo and placed proximate to the sample or subject to be studied (for example a human or an animal) and within the field of view (FOV) of one or more FECs.

Under appropriate conditions, the nuclear magnetism from one or more molecules in a sample or subject contained in one or more FEC coils can be made to feedback upon itself. Under such conditions we describe these molecule(s) as being in the super-radiant "state" (SR). The SR state is defined as being where $\tau R \le T_2$. Clinical MR machines cannot normally produce the conditions necessary to produce $\tau R \le T_2$. The present disclosure teaches, in addition to other teachings, methods and systems for achieving the SR state even for low concentrations of molecules in otherwise clinical conditions. These teachings include: use of a feedback enabled coil so that the active Q of one or more FEC coils included in, or added to, an MR machine can be made very high, and the use of an SSR, preferably ex vivo, to ensure that one or more molecules in the MR machine are in the SR state.

2. Signal Suppression

Further embodiments of the present disclosure permit the use of SR conditions to suppress the signal from one or more ensembles of nuclei in an NMR/MRI/MRS study, so that the signal from another set of nuclei can be more easily detected and used to produce a useful and tangible result, such as a MR image, or to achieve detection of a particular chemical species. Some implementations provide the suppression of the signal from fat in an in vivo MR study so that a superior image of water nuclei can be made by destroying the magnetization of the spins in the fat tissue.

Signal from fat and water is always present in an in vivo MR study. It is desirable to remove the signal from fat so as to better image the signal from water. To date this has been done by exploiting (a) the spectra differences between fat and water or (b) the difference in relaxation rates between fat and water.

One drawback of method (a) is that, for practical purposes, the spread in spectral frequencies of the fat and water nuclei result in their MR lines overlapping. Thus, destroying the magnetization in the fat leads to loss of water signal as some of that is destroyed as well. Also, any pulse that is tuned to "pick out" only the nuclei in fat must be quite long, leading to longer sequence times (TRs). Method (b) suffers from requiring a considerable time lag as the imaging study must wait for $\ln_2 *T_{1_{fat}}$ before the signal from fat is sufficiently removed. Not only does this introduce a time lag, but during this period some signal from the water inevitably decays leading to poorer images.

Embodiments of the present disclosure overcome these drawbacks by exploiting properties of the superradiant condition. Specifically, such embodiments permit the signal from of a given ensemble of nuclei, such as protons in fat, to be destroyed very rapidly, such as in times less than $T_2$. This can result in the production of widely separated pulses between nuclei in two or more different molecules or types of molecules, such as between protons in water and fat, so that the signal from one can be suppressed to allow superior images of the other to be made.

Applicant has discovered that the peak time position of an SR pulse is a function, amongst other factors, of the number, Larmor frequency, and $T_2$ of a given set of nuclei. These vary widely for the same nuclei in different molecules. For example, the $^1H$ $T_2$ of water is ~800 msec in vivo. But for fat the $^1H$ $T_2$ is ~80 msec. There is a chemical shift difference between the precessional frequency of protons in fat and water as well, of ~3.5 ppm at 3 T. Finally, in an in vivo environment, the amount of water and fat is different so their response to SR conditions is different.

When the system is in the SR condition the response of the system to an inversion of the nuclear magnetism to an angle greater than 90 degrees is a pulse rather than a Free Induction Decay (FID). In the limit where $T_2$ is large($T_2 \gg \tau_R$) and the inversion is close to 180 degrees using equation 16 the peak-time of the pulse can be written as:

$$t_o = \tau_R \ln_2$$

Typically, $t_o < T_2$, meaning that the magnetization of a given set of nuclei can be driven very quickly to a desired angle with respect to the main magnetic field ($B_o$) of the MR system.

Furthermore, an SR pulse can be halted, or "cut", at any time via the imposition of a field gradient sufficient in strength to suppress SR conditions so that $T_2 < \tau_R$. As a non exclusive example, the SR pulse due to fat can be cut where it crosses the x axis, i.e. where $M_z(fat)=0$. Hence in this circumstance the magnetization from the fat has been completely destroyed.

In an in vivo study, the SR pulse from water has a different time constant from that of fat. As described above, this is because there are different amounts of water than fat in the coil. In addition, the chemical shifts of fat and water differ slightly. The SR time constant difference can be emphasized by centering the resonant frequency of the resonator on either the fat or water frequency. Hence the water $^1H$ magnetization can be made to be very far from the x axis when the gradient is imposed, i.e., a very large fraction of the water magnetization can still be along the z axis while that from the fat is at z~0.

In this circumstance, images can be made from water with minimal interference from unwanted fat signal. The image can begin on timescales $\sim \tau_R$, which are much faster than $\sim T_1$ as required by the method (b) described above.

Figure 5:
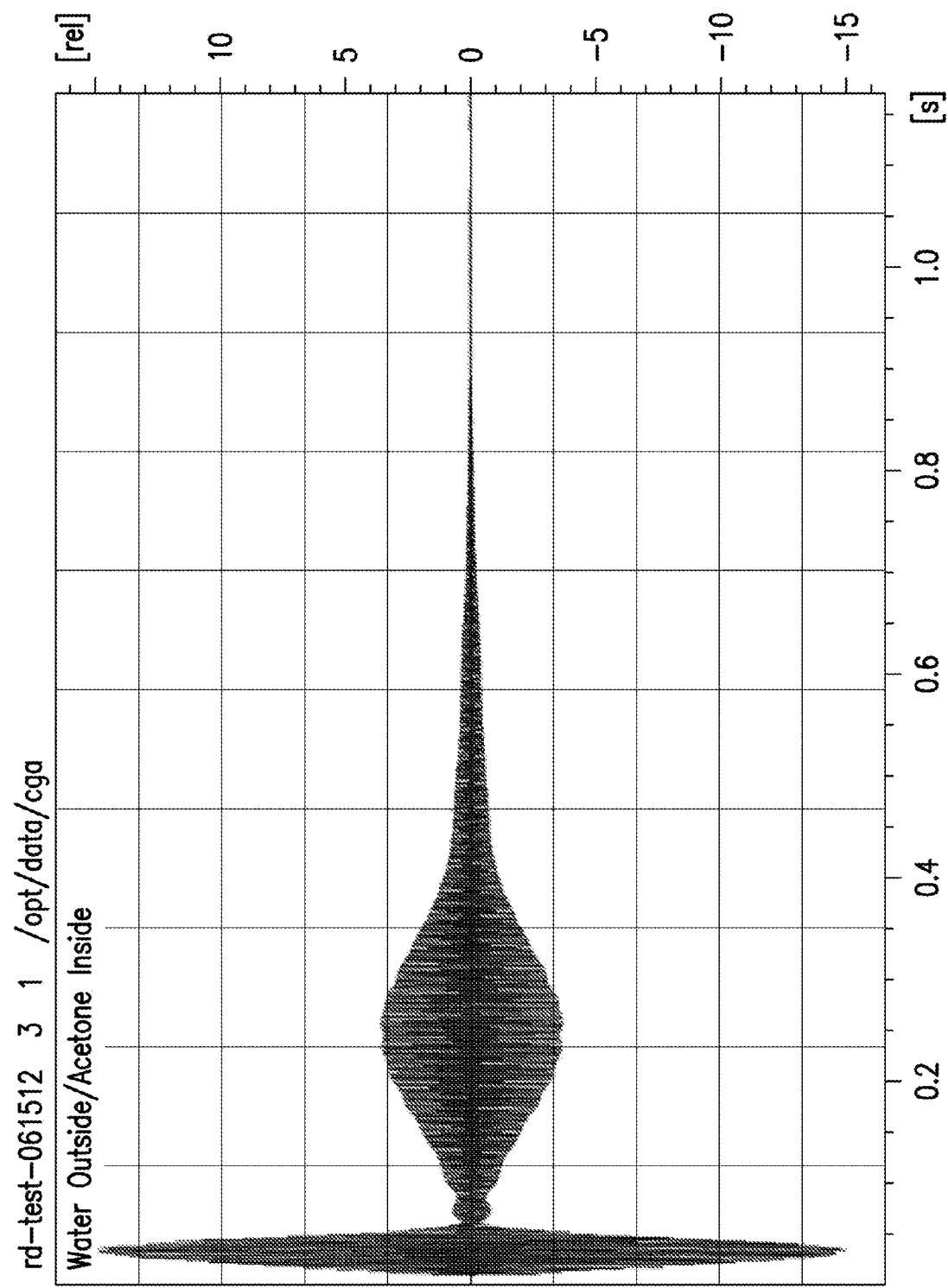
FIG. 5 depicts a signal vs. time chart for a coaxial tube containing water (outside) and acetone (inside).

A further example of the separation of SR pulses is shown in FIG. 5 for acetone and water. Water was placed in the inner compartment of a coaxial NMR tube, acetone in the outer. In a 700 MHz magnet the 1H spins in each molecule were simultaneously flipped using a pi pulse. The resultant SR pulses are easily distinguished from one another. As will be appreciated by those of skill in the art, these embodiments can be combined with and/or employ equipment, methods, machine readable programs and techniques described elsewhere herein.

Thus, provided herein is a method for suppressing nuclear magnetization from one or more set of nuclei, that includes:
 a) providing a magnetic resonance device including (i) a main magnet for providing a background magnetic field along a first direction, (ii) at least one radio-frequency coil, and (iii) at least one gradient coil that can be controlled to define at least one region of interest;
 b) introducing a sample or subject to the MR device
 c) creating SR conditions for one or more set of nuclei in the sample or subject, for example, the fat in an in vivo sample or subject could be made to be in SR conditions, while water is not, or vice versa. Optionally an FEC and/or SSR can be used to produce these conditions
 d) inverting all magnetizations in the sample or subject, preferably but not exclusively to 180 degrees
 e) by manipulating the FEC, induce one set of magnetization will be driven to be driven to preferably 90 degrees while others remain at a much different angle, preferably 180. The magnetization at 90 can then be completely destroyed by imposing a field gradient while those at 180 remain undisturbed.
 f) Make image of desired FOV It will be appreciated that the above described technique can be employed in various contexts to select signal from any suitable desired ensemble of spins. The magnetization of any desired species can effectively be destroyed, for example, via the imposition of a field gradient sufficient in strength to suppress SR conditions for that species so that $T_2 < \tau_R$.

3. Reduced FOV

Further embodiments of the present disclosure provide using SR pulses to selectively "light up", or obtain useful signal data (e.g., suitable for forming images, etc.) from one portion of a volume that is being imaged within a larger region of interest that may be excited by a given RF pulse. This controlled, and in some instances, reduced field of view ("FOV") allows data capture to be carried out using signal obtained in only one desired region of the entire volume from which signal would have otherwise been obtained when performing typical imaging operations previously known in the art. This reduced imaging time can thus permit a radiologist or other investigator to effectively "zoom in" on one portion of a larger potential region of interest ("ROI") rather than having to view signal from the entire ROI. It will be appreciated herein that the ROI could simply be considered to be the particular area of interest to be studied rather than the larger volume within the RF coil that could be studied.

Techniques for reducing FOV while using RF pulses do exist, wherein a linear field gradient is imposed on the subject or sample and then using frequency selective rf pulses to select a "slice" from that volume. For example, by slicing in 3 dimensions a reduced FOV in the form of a cube can be created.

However, Applicant has come to appreciate that these previously existing methods suffer from a number of drawbacks. First, the RF pulses must be "soft"—that is to say, relatively long pulses of high intensity to achieve reasonable levels of spatial selection. These pulses can be of such long duration that local $T_2$ relaxation can begin to degrade sample or subject magnetization during the process. Also, spatial resolution of the reduced FOV produced in this manner can often be on the order of a cm or more; too large for many in vivo applications where the organ or anatomy of interest may be smaller than that.

The present methods, and related systems and computer programs overcome these drawbacks by exploiting properties of the superradiant pulse. Specifically, the SR pulse is very sensitive to the presence of field gradients to select out one region in which transverse magnetization can be permitted to survive. Thus the resolution of the FOV in the present technique is a function of the resolution of the field gradient; whereas in existing techniques it is a function of the resolution of the field. This allows greater control over the reduced FOV parameters.

More specifically, Applicant has discovered and appreciated that the conditions for propagation of an SR pulse are very sensitive to local field gradients.

The superradiant condition is defined as $\tau_R < T_2$. Under these conditions the response of the system to an inversion of the nuclear magnetism to an angle greater than 90 degrees is a pulse rather than a Free Induction Decay (FID).

In a region of space where $t_o < T_2$, then the SR pulse propagates with a width and peaktime according to Equations 13 and 19. In a region of space where $t_o > T_2$ no pulse propagates. Assuming that the initial state of the magnetization is complete inversion, then after a time $t < t_o < T_2 < T_1$, inside the volume a non zero transverse magnetization will develop. Outside this region, where $t_o > T_2$, then the magnetization is still completely inverted with no or very little transverse magnetization.

Figure 6:
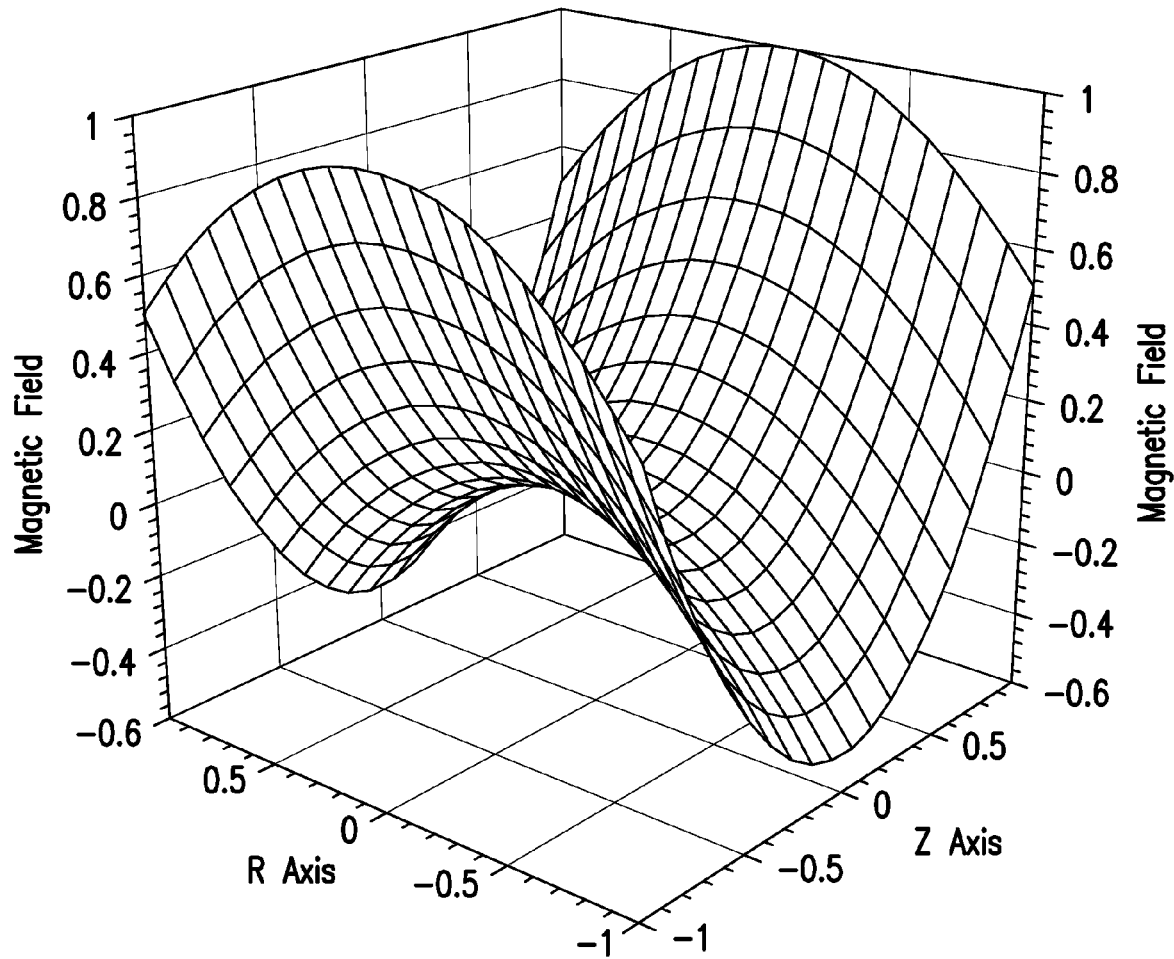
FIG. 6 is an illustrative field map showing where the local gradient is very strong except in one region of space.

Spatially dependent field gradients are well known in NMR/MRI. Second order shims produce field maps where the local gradient is very strong except in one region of space (FIG. 6). This region can be widened/narrowed, or moved in 3D, by adjusting the shim coils of the magnet.

Once Mxy has been created in a specific region of space, standard sequences can be used to produce the desired image. In particular, the use of an imaging sequence that employs one or more field gradients is preferred as the establishment of even a weak gradient will generally impose conditions of $t_o > T_2$ everywhere in the volume. This has the effect of halting or "cutting" the SR pulse inside the reduced FOV, with no effect on remaining longitudinal magnetization outside the reduced FOV.

Figure 7:
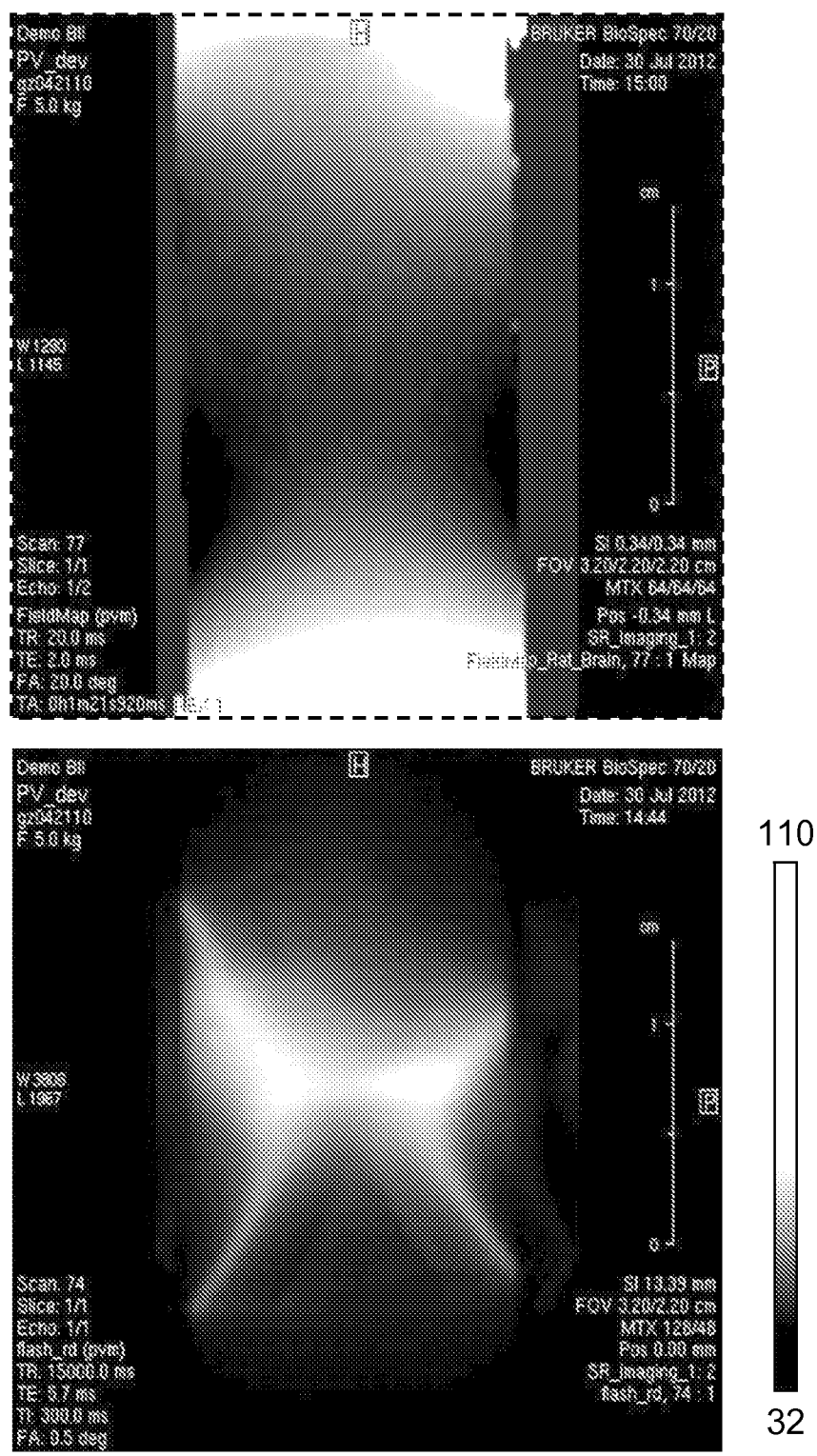
FIG. 7 shows examples of an image made using SR pulses.

FIG. 7 shows examples of an image made from Mxy produced in local regions by establishing SR conditions in some parts of the sample or subject while destroying it in others. Specifically, FIG. 7 shows that, as expected, images made in this manner closely follow the local field gradient. Thus, by controlling the higher order shims it is possible to constrain the image to a reduced volume. The sample was a 20 mm diameter water cylinder inside a 7 T magnet, probe Q~300. The magnet was well shimmed and then the z2 gradient was slightly perturbed to produce the field map shown in the upper half of the figure. Then the proton magnetization was inverted to 180 degrees. A crusher gradient removed any remaining transverse magnetization, after which a "kick" pulse of <0.1 degree was applied to the sample. This produced an SR pulse with a peak time ~200 msec. The image at the bottom of the figure was made by "cutting" the SR pulse at ~200 msec and then imaging the resulting transverse magnetization using a standard FLASH sequence. The resulting image follows the field map produced by the z2 gradient closely.

4. RF Coil Implementations

SR conditions have been heretofore largely unknown in clinical MR because the requisite conditions—high magnetic field and/or high probe quality factor Q—are not produced by commercially available MR machines known in the art. SR conditions are a more common phenomenon in high field NMR studies, where they are generally considered an annoyance as their best known effect is to broaden the spectroscopic lines of the nuclei under observation. SR conditions are not desirable when one is trying to resolve the identity of many different molecules in a single sample, which is the goal typical of many NMR studies. The present disclosure recognizes that SR conditions can be a benefit when the goal is the identification and quantification of a single molecule to the exclusion of others in the field of view. By adding the notion of control, through the use of a Feedback Enabled Coil (FEC) and a Supplementary Spin reservoir (SSR), SR enables powerful feedback-driven MR methods.

As discussed elsewhere herein, SR occurs when $\tau_R \leq T_2$ conditions are arranged for one or more set of nuclei, where $\tau_R = 1/\gamma\beta|\sin\alpha|M_o$ . . . . In this expression, $\beta$ and $\alpha$ are the magnitude and phase of the gain factor generated by a feedback enabled coil, $\gamma$ is the gyromagnetic ratio, and $M_o$ is the maximum value of the magnetization, which will be equal to thermal polarization.

As noted above, MR scanners known heretofore in the art are not generally capable of producing the conditions required for SR. In addition, they are not typically set up as feedback-enabled devices. One way to overcome these factors is to build a coil capable of producing feedback even under clinical MR conditions. The coil/electronics are preferably able to adjust the phase of the magnetization as well as the gain of the feedback. We term such a coil a Feedback Enabled Coil (FEC). Schematics of exemplary hardware are presented below.

Figure 8:
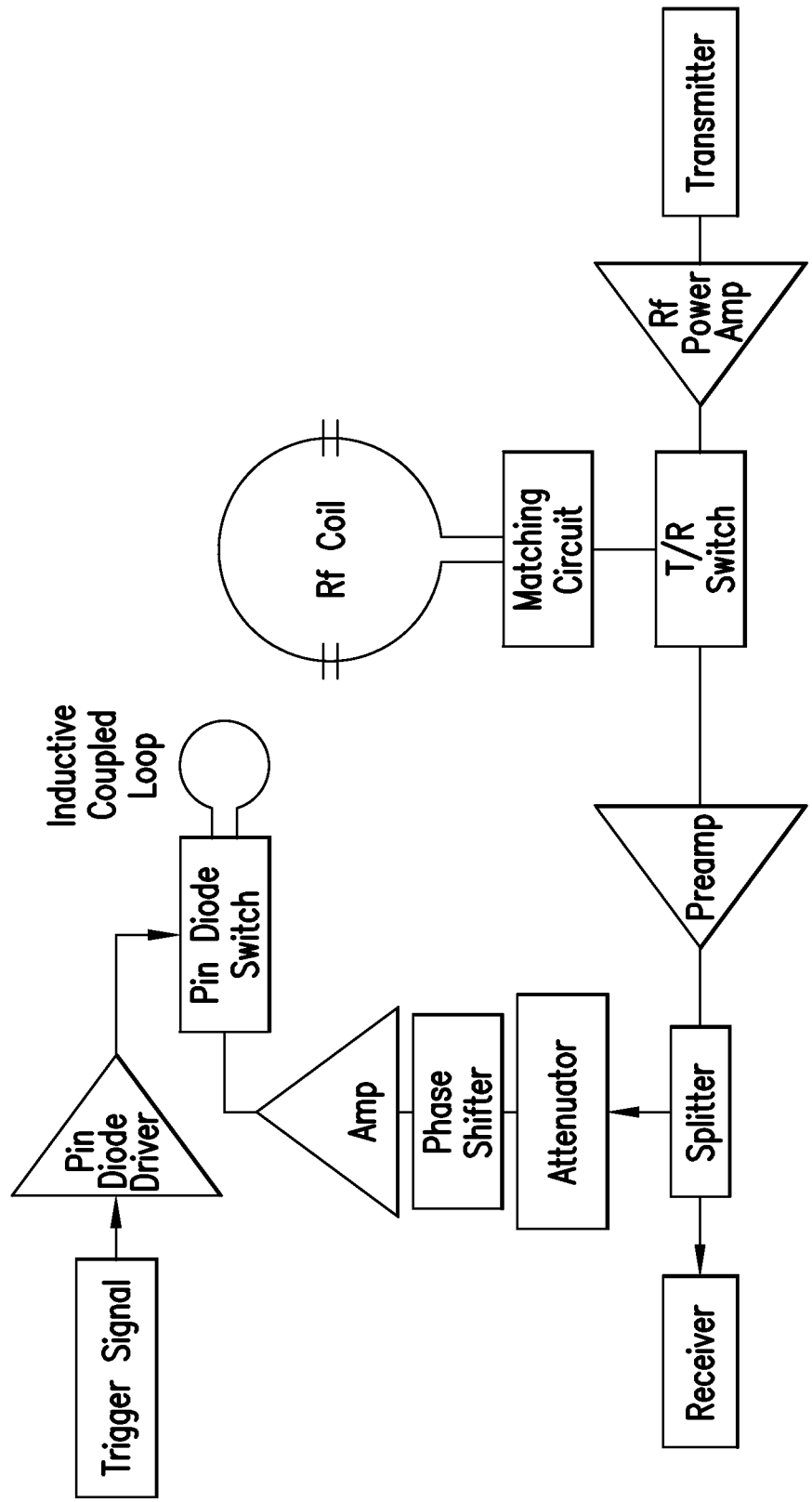
FIG. 8 is an example of a feedback system known in the art.

An example of a feedback system known in the art is shown in FIG. 8. In this particular case, a transmit/receive surface coil is employed in a typical manner. In principle, any RF coil can be used, even receive-only coils, thus we will refer to this coil as the RF coil. The output of the preamp is split off and fed into a feedback circuit. After applying the appropriate attenuation and phase setting/shifting, the output of the feedback circuit is then fed back into the RF coil via an inductively coupled loop. In principle, the gain and phase may be any value with the potential to shorten the radiation damping constant to any desired value. Also, as a pin diode switch is employed, radiation damping can be turned on and off under system control via a pulse sequence.

However, the circuit of FIG. 8 has two major shortcomings for a practical implementation of radiation damping. The inductively coupled loop is loosely coupled to the RF coil. This is necessary to prevent the output of the feedback circuit to adversely affect the tune and match of the RF coil. Consequently, greater power is required by the feedback circuit then is necessary. To achieve small radiation damping constants, an improvement in efficiency is necessary to reduce power requirements. A second shortcoming is that the signal coming from the RF coil has two significant components. One component is the RF signal arising from the magnetization of the spin system. The second component is the signal generated by the feedback circuit. Fortunately these two components are normally phase shifted by 90°, so that it is possible to maintain a stable mode of operation for the feedback circuit. While the inefficiency of the circuit helps to promote stability, the circuit will be sensitive to phase. With sufficient gain, there is the danger of creating positive feedback.

Figure 9:
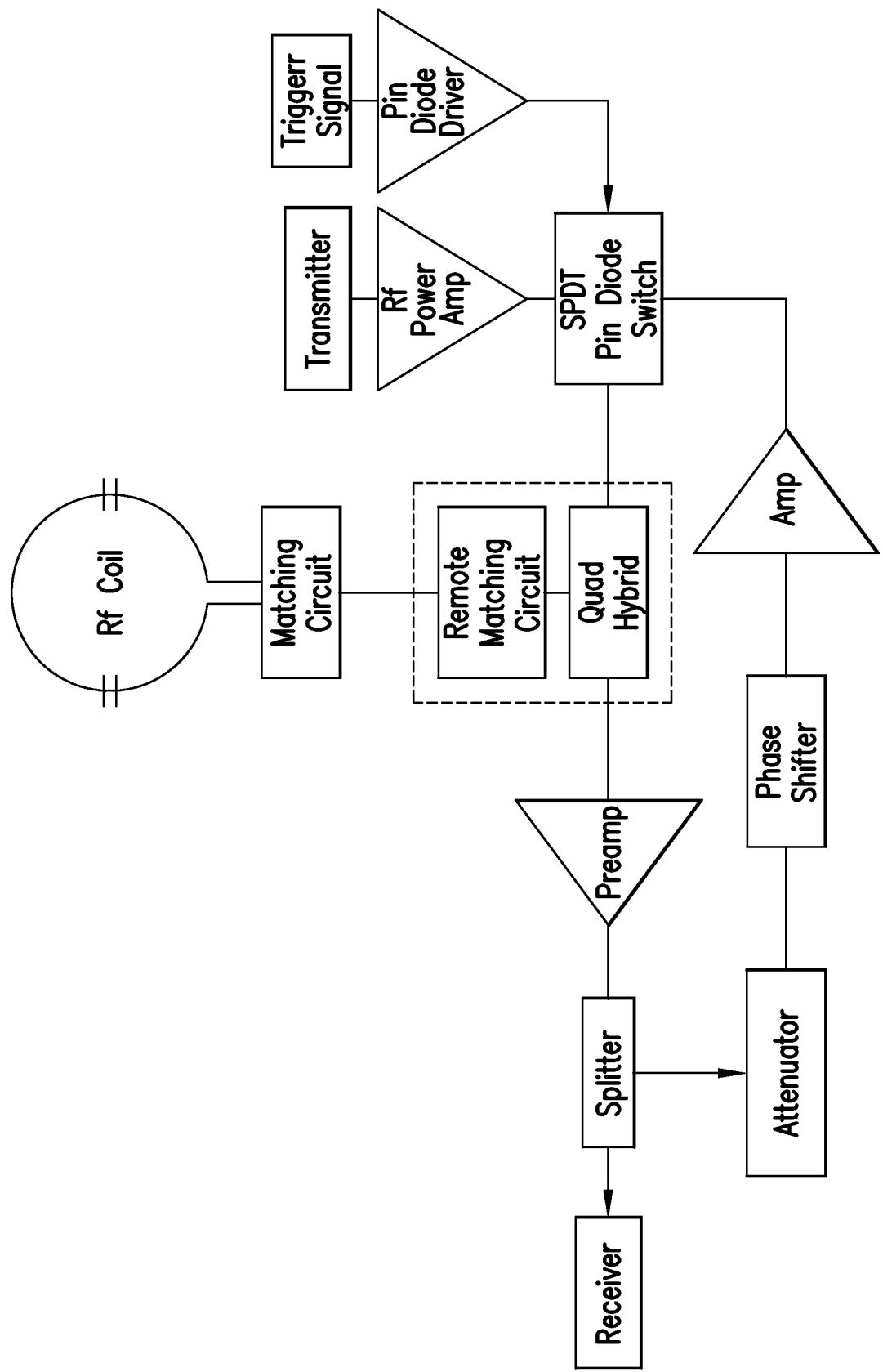
FIG. 9 is an example of a feedback system for a FEC coil provided in accordance with the disclosure.

Applicant has developed a circuit design which overcomes these shortcomings as shown in FIG. 9. A component of the embodiment of FIG. 9 is the quadrature hybrid block (indicated with a dashed block), which causes reflected power from the RF coil to appear on the output of this circuit but not upon the input. This block can have different designs depending upon the type of RF coil employed. The reflected power from the NMR coil will again have two components, one component from the spin system and the other component will be reflected power from mismatch with the coil. Additional remote tuning/matching circuit(s) inside the quad hybrid block can minimize the reflected power due to any impedance mismatches while the NMR signal which arises from the spin system is not affected. This can minimize the undesirable component while maintaining an efficient coupling to the coil. If the embodiment of the RF coil is a receive-only coil, then the circuit is further simplified by removing the transmitter and RF power amp from the figure. The design of the quadrature hybrid block can vary depending upon the type of coil used. If a surface coil (or any coil that is considered linear) is used, then the quad hybrid block utilizes two quadrature hybrids and one remote matching circuit. If a quadrature coil is used then the quadrature hybrid block includes two remote matching circuits and one quadrature hybrid. This design is scalable to parallel imaging coil arrays.

EXAMPLE

Figure 10C:
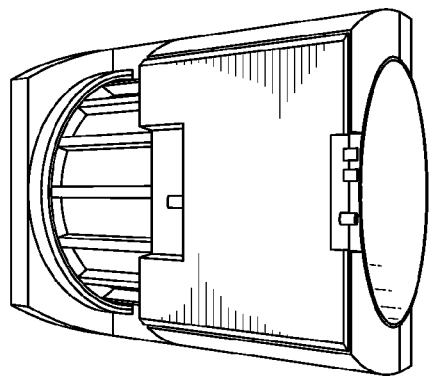
FIGS. 10 A-C are depictions of a FEC coil and supporting hardware provided in accordance with the disclosure.
Figure 10B:
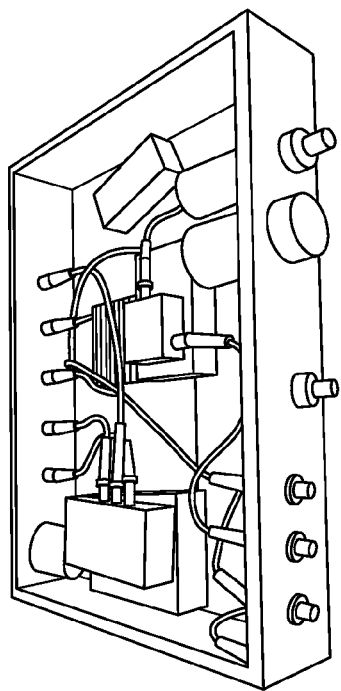
Figure 10A:
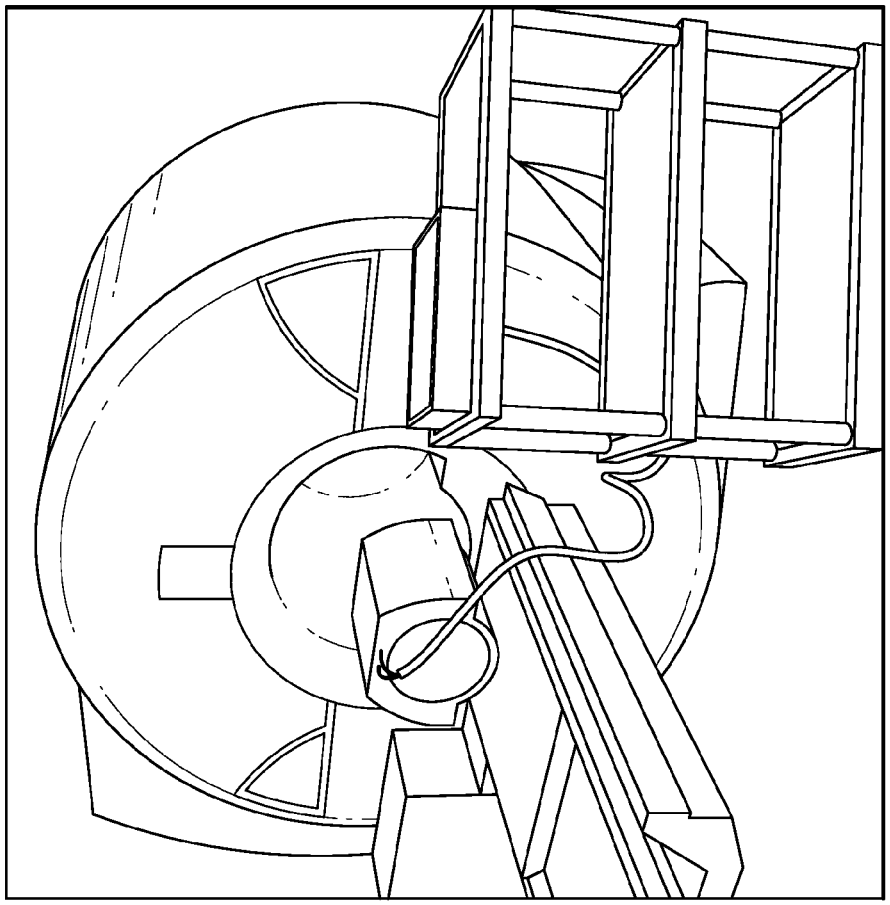
Figure 11:
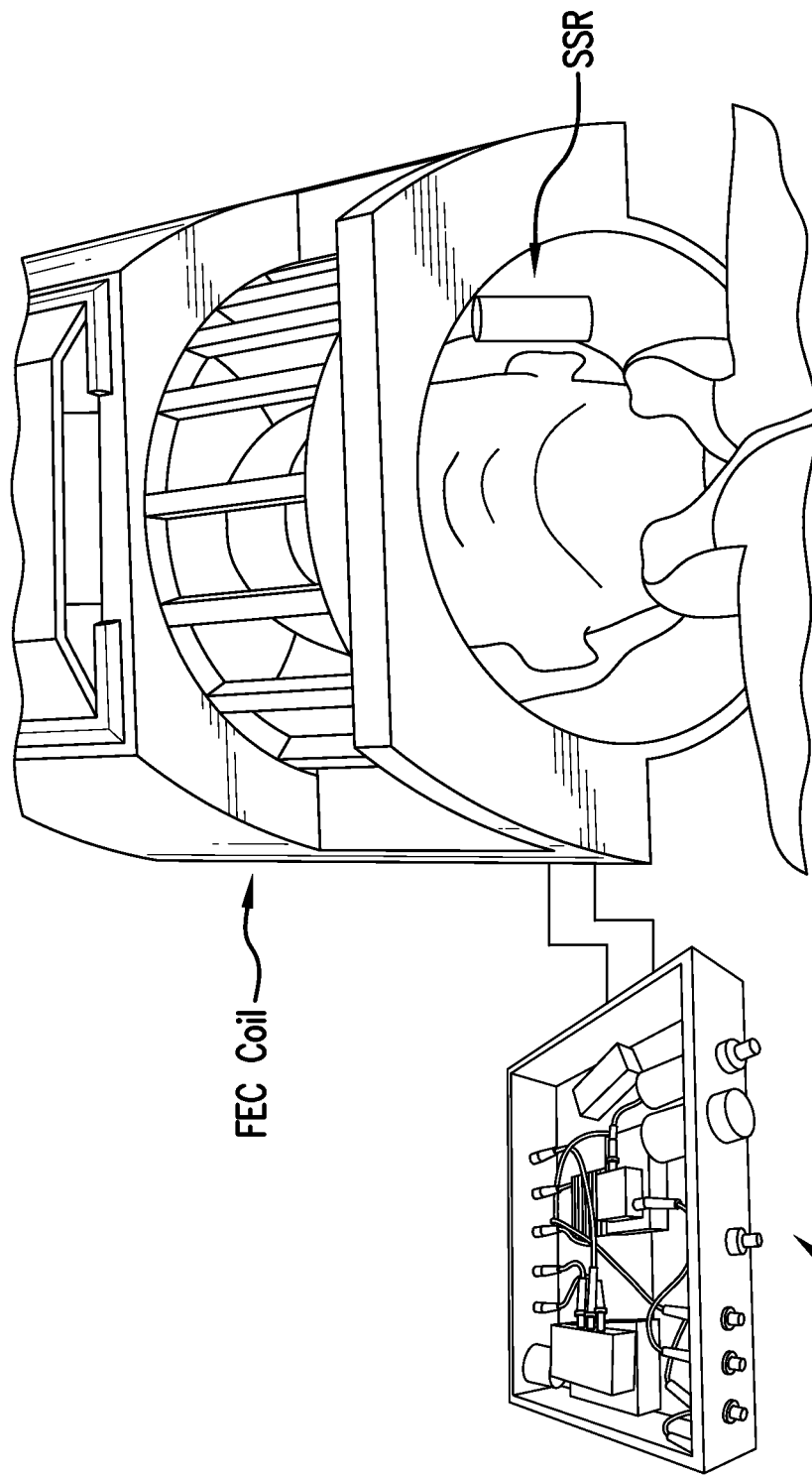
FIG. 11 depicts a subject inside a Feedback Enabled Coil (FEC) with an Supplementary Spin reservoir (SSR) located nearby and inside the Field of View (FOV) of the same FEC.

For the purpose of this disclosure, a commercially available head coil (e.g., FIG. 9A) (e.g., single channel) for operation on a 1.5T Siemens Avanto MRI scanner (FIG. 10B) can be used, and modified to be operated using a feedback circuit with a quadrature hybrid block as set forth above with respect to FIG. 9, such as the illustrative embodiment depicted in FIG. 10C. A low power amplifier can be used initially (~10 watts) to test the feedback circuit, to insure against positive feedback, and to obtain initial results.

All statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Descriptions herein of circuitry and method steps and computer programs represent conceptual embodiments of illustrative circuitry and software embodying the principles of the disclosed embodiments. Thus the functions of the various elements shown and described herein may be provided through the use of dedicated hardware as well as hardware capable of executing software in association with appropriate software as set forth herein.

In the disclosure hereof any element expressed as a means for performing a specified function is intended to encompass any way of performing that function including, for example, a) a combination of circuit elements and associated hardware which perform that function or b) software in any form, including, therefore, firmware, microcode or the like as set forth herein, combined with appropriate circuitry for executing that software to perform the function. Applicants thus regard any means which can provide those functionalities as equivalent to those shown herein.

Similarly, it will be appreciated that the system and process flows described herein represent various processes which may be substantially represented in computer-readable media and so executed by a computer or processor, whether or not such computer or processor is explicitly shown. Moreover, the various processes can be understood as representing not only processing and/or other functions but, alternatively, as blocks of program code that carry out such processing or functions.

The methods, systems, computer programs and mobile devices of the present disclosure, as described above and shown in the drawings, among other things, provide for improved magnetic resonance methods, systems and machine readable programs for carrying out the same. It will be apparent to those skilled in the art that various modifications and variations can be made in the devices, methods, software programs and mobile devices of the present disclosure without departing from the spirit or scope of the disclosure. Thus, it is intended that the present disclosure include modifications and variations that are within the scope of the subject disclosure and equivalents.

What is claimed is:

1. A method for performing a magnetic resonance protocol comprising:
   a) providing a magnetic resonance device including (i) a main magnet for providing a background magnetic field along a first direction, (ii) at least one radio-frequency coil, and (iii) at least one gradient coil configured to be controlled to define a region of interest;
   b) introducing a sample or subject to be studied into the region of interest, the sample or subject including (i) a first set of nuclei of interest from which a magnetic resonance signal is desired and (ii) a second set of nuclei from which a magnetic resonance signal is not desired;
   c) introducing into the magnetic resonance device at least one supplemental spin reservoir ("SSR") distinct from the sample or subject, the SSR including a plurality of molecules having nuclei substantially identical to the nuclei in the first set of nuclei;
   d) introducing radio frequency ("RF") pulses into the sample or subject to be studied to energize nuclei in the sample or subject;
   e) inducing feedback between the at least one radio frequency coil and (i) the first set of nuclei and (ii) the second set of nuclei so as to cause the vector direction of the nuclear magnetization of the nuclei in the first and second sets of nuclei to differ substantially from each other; and
   f) detecting a magnetic resonance signal preferentially from the first set of nuclei using the at least one radio frequency coil, wherein the magnetic resonance signal detected from the first set of nuclei partially originates from the SSR.

2. The method of claim 1, further comprising analyzing the magnetic resonance signal detected from the first set of nuclei so as to produce at least one of (i) an image, (ii) dynamic flow data, (iii) perfusion data, (iii) spectroscopic identity of chemical species, (iv) physiological data, and (v) metabolic data.

3. The method of claim 1, where the sample or subject is a living creature.

4. The method of claim 3, wherein the first set of nuclei include protons in water and the second set of nuclei include protons in fat.

5. The method of claim 3, wherein the first set of nuclei include protons in fat and the second set of nuclei include protons in water.

6. The method of claim 1, wherein the at least one radio frequency coil is configured to induce or control feedback specifically for molecules contained in the SSR.

7. The method of claim 1, wherein at least one transmit coil is used to deliver the RF pulses and further wherein at least one distinct receive coil is used to detect the magnetic resonance signal from the first set of nuclei.

8. A method for performing a magnetic resonance protocol comprising:
   a) providing a magnetic resonance device including (i) a main magnet for providing a background magnetic field along a first direction, (ii) at least one radio-frequency coil, and (iii) at least one gradient coil configured to be controlled to define a region of interest;
   b) introducing a sample or subject to be studied into the region of interest;
   c) introducing into the MR device at least one supplemental spin reservoir ("SSR") distinct from the subject or sample, the SSR including a plurality of molecules having nuclei of interest from which a magnetic resonance signal is desired;
   d) introducing RF pulses into the sample or subject to energize nuclei in the sample or subject;
   e) inducing feedback between the at least one radio frequency coil and (i) nuclei in the sample or subject and (ii) the nuclei of interest in the SSR so as to cause the vector direction of the nuclear magnetization of the nuclei in the sample or subject and the nuclei of interest in the SSR to rotate to a desired angle with respect to the first direction of the background magnetic field; and
   f) detecting magnetic resonance signals from at least one of the nuclei of interest in the SSR and the sample or subject.

9. The method of claim 8, further comprising processing the magnetic resonance signals from the subject or sample to produce at least one of: (i) an image, (ii) dynamic flow data, (iii) perfusion data, (iii) spectroscopic identity of chemical species, (iv) physiological data, and (v) metabolic data.

10. The method of claim 9, where at least one gradient magnetic field is manipulated to suppress feedback between the at least one radio frequency coil and nuclei in a first physical region of the sample or subject.

11. The method of claim 8, where the nuclei of interest include at least one of $^1$H, $^{13}$C and $^{15}$N.

12. The method of claim 9, where the subject is a living creature.

13. The method of claim 9, where the at least one radio frequency coil is configured to induce or control feedback specifically for molecules contained in the SSR.

14. The method of claim 9, wherein at least one transmit coil is used to deliver the RF pulses and further wherein at least one distinct receive coil is used to detect the magnetic resonance signal from the first set of nuclei.

15. The method of claim 9, further comprising:
   a) employing RF pulses to rotate a further set of nuclear magnetization to a desired angle for a second set of nuclei of interest;
   b) detecting a signal relating to the pulse of transverse magnetization originating from the second set of nuclei of interest; and
   c) processing the signal to form a data set relating to the presence of the second set of nuclei in the sample or subject.

16. The method of claim 15, where an image formed from the second set of nuclei in the sample or subject is used to spatially locate an image formed from the first set of nuclei.

17. A method for performing quantitative analysis of the amount of a molecule in a sample or subject comprising:
   a) providing a magnetic resonance ("MR") device including (i) a main magnet for providing a background magnetic field along a first direction, (ii) at least one radio frequency coil, and (iii) at least one gradient coil configured to be controlled to define at least one region of interest;
   b) introducing into the MR device at least one supplemental spin reservoir ("SSR") distinct from the subject or sample, the SSR including a plurality of molecules having nuclei of interest from which a magnetic resonance signal is desired;
   c) adjusting the circuitry of the at least one radio-frequency coil in order to induce feedback between the nuclear magnetization of the nuclei of interest within the SSR and the at least one radio frequency coil;
   d) introducing RF pulses into the SSR so that the magnetization of the nuclei of interest within the SSR is rotated to a first angle greater than ninety degrees;
   e) receiving a magnetic resonance signal from the nuclei of interest within the SSR indicative of a first superradiant ("SR") pulse;
   f) analyzing the first ("SR") pulse that results from step (e) to determine the peaktime and width of the SR pulse;
   g) introducing a sample or subject to be studied into the region of interest;
   h) introducing RF pulses into the sample or subject and the SSR so that the vector direction of the magnetization of the nuclei of interest is rotated to the first angle;
   i) analyzing a second SR pulse that results from step (h) to determine the peaktime and width of the second SR pulse; and
   j) subtracting the first SR pulse from the second SR pulse to produce quantitative information as to the amount of nuclei of interest in the sample or subject.

18. The method of claim 17, where the nuclei of interest are present in serotonin in the sample or subject.

* * * * *

UNITED STATES PATENT AND TRADEMARK OFFICE
CERTIFICATE OF CORRECTION

| | |
|---|---|
| PATENT NO. | : 9,014,785 B2 |
| APPLICATION NO. | : 14/188410 |
| DATED | : April 21, 2015 |
| INVENTOR(S) | : Neal Kalechofsky et al. |

It is certified that error appears in the above-identified patent and that said Letters Patent is hereby corrected as shown below:

On the title page, item (63) "Related U.S. Application Data" should read as follows:

"Continuation-in-Part of application No. 13/844,446, filed on Mar. 15, 2013, which is a continuation-in-part of application No. 13/623,759, filed on Sep. 20, 2012, now abandoned, which is a continuation of application No. PCT/US2012/030384, filed on Mar. 23, 2012, application No. 14/188,410, which is a continuation of application No. 13/844,446."

Signed and Sealed this
Fifteenth Day of September, 2015

Michelle K. Lee
*Director of the United States Patent and Trademark Office*